US008509879B2

(12) United States Patent
Durkin et al.

(10) Patent No.: US 8,509,879 B2
(45) Date of Patent: Aug. 13, 2013

(54) APPARATUS AND METHOD FOR WIDEFIELD FUNCTIONAL IMAGING (WIFI) USING INTEGRATED STRUCTURED ILLUMINATION AND LASER SPECKLE IMAGING

(75) Inventors: Anthony J. Durkin, Irvine, CA (US);
David Cuccia, Costa Mesa, CA (US);
Bruce J. Tromberg, Irvine, CA (US);
Amaan Mazhar, Irvine, CA (US);
Bernard Choi, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 1294 days.

(21) Appl. No.: 12/016,918

(22) Filed: Jan. 18, 2008

(65) Prior Publication Data

US 2009/0118622 A1    May 7, 2009

Related U.S. Application Data

(60) Provisional application No. 60/985,872, filed on Nov. 6, 2007.

(51) Int. Cl.
*A61B 6/00* (2006.01)

(52) U.S. Cl.
USPC ............ 600/473; 600/476; 600/479; 600/407

(58) Field of Classification Search
USPC ................. 600/473, 407, 476, 479; 382/128; 250/459.1; 359/368
See application file for complete search history.

(56) References Cited

U.S. PATENT DOCUMENTS

| | | | | |
|---|---|---|---|---|
| 6,208,415 | B1 * | 3/2001 | De Boer et al. | 356/450 |
| 2003/0002028 | A1 * | 1/2003 | Rice et al. | 356/39 |
| 2006/0155195 | A1 * | 7/2006 | Maier et al. | 600/476 |
| 2006/0184043 | A1 * | 8/2006 | Tromberg et al. | 600/476 |
| 2006/0268241 | A1 * | 11/2006 | Watson et al. | 353/94 |

OTHER PUBLICATIONS

Dunn, A. K. Simultaneous imaging of total cerebral hemoglobin concentration, oxygenation, and blood flow during functional activation, Optics Letters, vol. 28, 1, Jan 2003, pp. 28-30.*
Briers, J.D., Laser Doppler, speckle, and related techniques for blood perfusion mapping and imaging, Physiological Measurement, 22 (2001), R35-R66.*
MacKinnon, N., et al, Spectrally Programmable light engine for in vitro or in vivo molecular imaging and spectroscopy, Applied Optics, Apr. 10, 2005, vol. 44, No. 11. pp. 2033-2040.*
Barlow, A.L., et al, Quantization of Widefield Fluorescence Imaging Using Structured Illumination and Image Analysis Software, Microscopy Research and Technique, 70: 76-84 (2007).*
Ventalon, C., et al, "Dynamic speckle illumination microscopy with translated versus randomized speckle patterns," Opt. Express 14, 7198-7209 (2006).*

* cited by examiner

*Primary Examiner* — Unsu Jung
*Assistant Examiner* — Daniel Huntley
(74) *Attorney, Agent, or Firm* — Daniel L. Dawes; Marcus C. Dawes

(57) ABSTRACT

An apparatus for wide-field functional imaging (WiFI) of tissue includes a spatially modulated reflectance/fluorescence imaging (SI) device capable of quantitative subsurface imaging across spatial scales, and a laser speckle imaging (LSI) device capable of quantitative subsurface imaging across spatial scales using integrated with the (SI) device. The SI device and LSI device are capable of independently providing quantitative measurement of tissue functional status.

9 Claims, 20 Drawing Sheets

Table 2 – Instrument Designs and Features

| Instrument | Key Features | Field of View | Acquisition Time | Embodiment | Extracted Characteristics | Derived Characteristics | Biophysical Parameters Under Study |
|---|---|---|---|---|---|---|---|
| Real-Time Optical Neuroimaging (Instrument 1) | *Preclinical* <br> • First combined MRI/LSI system <br> • Blood flow <br> • Neural activity <br> • Hemodynamics | 1 cm × 1 cm | 50 ms (20 fps) | Multi-axis linear stage | $\mu_a(x,y,t)$ <br> $\mu_s'(x,y,t)$ <br> $BF(x,y,t)^*$ | $stO_2(x,y,t)$ <br> $MRO_2(x,y,t)^*$ | • Cellular swelling ($\mu_s'$) during seizure <br> • $MRO_2$ dynamics associated with seizure and ischemic stroke |
| Small Animal Imaging & Tomography (Instrument 2) | *Preclinical* <br> Quantitative depth resolved fluorescence molecular imaging | 10cm × 10cm | 1-10 min | Light-tight enclosure | $\mu_a(x,y,z,t)$ <br> $\mu_s'(x,y,z,t)$ <br> $F(x,y,z,t)^*$ <br> $BF(x,y,t)^*$ | $stO_2(x,y,t)$ <br> $MRO_2(x,y,t)^*$ | • $\mu_a$, $stO_2$ and $MRO_2$ dynamics during subcutaneous tumor growth and chemotherapy <br> • Vascular permeability assessment with exogenous fluorescence agents <br> • $MRO_2$ mapping of chronic ischemic wounds |
| Clinic-Friendly (Instrument 3) | *Clinical* <br> Single-image Spectroscopy | 10cm × 10cm | 1 fps | Articulated arm | $\mu_a(x,y,z,t)$ <br> $\mu_s'(x,y,z,t)$ <br> $BF(x,y,z,t)^*$ <br> $F(x,y,z,t)^*$ | $stO_2(x,y,z,t)$ <br> $MRO_2(x,y,z,t)^*$ <br> $C_{lip}(x,y,z,t)$ <br> $C_{wat}(x,y,z,t)$ <br> $C_{mel}(x,y,z,t)$ <br> $OY(x,y,z,t)$ | • Correlation of $\mu_a$, $MRO_2$ and $C_{wat}$, $C_{mel}$ values with efficacy of part wine stain laser therapy <br> • Correlation of $stO_2$, $MRO_2$, $C_{lip}$, $C_{wat}$, $C_{mel}$ values with benign pigmented lesions and malignant melanoma <br> • $\mu_a$, $\mu_s'$, $MRO_2$, and OY mapping to guide tumor surgical resection <br> • $\mu_a$ mapping for nanoparticle-enhanced tumor imaging and therapy |

\* F = fluorescence, BF = blood flow, $MRO_2$ = metabolic rate of oxygen consumption, $C_{lip}$ = lipid content, $C_{mel}$ = melanin content, $C_{wat}$ = water content

Fig. 14

APPARATUS AND METHOD FOR WIDEFIELD FUNCTIONAL IMAGING (WIFI) USING INTEGRATED STRUCTURED ILLUMINATION AND LASER SPECKLE IMAGING

RELATED APPLICATIONS

The present application is related to U.S. Provisional Patent Application Ser. No. 60/985,872, filed on Nov. 6, 2007, which is incorporated herein by reference and to which priority is claimed pursuant to 35 USC 119.

GOVERNMENT RIGHTS

This invention was made with government support under grant RR001192 awarded by the National Institutes of Health. The government has certain rights in the invention.

BACKGROUND OF THE INVENTION

1. Field of the Invention

The invention relates to the field of medical imaging using light.

2. Description of the Prior Art

Due to its relatively low cost and ease of implementation, optical imaging is an attractive technology to study intrinsic signals associated with endogenous chromophores as well as targeted exogenous probes. With the explosive growth in available molecular reporter strategies for studying fundamental biophysical processes, there has been a paradigm shift in research efforts from ex vivo destructive evaluation to in vivo analysis, allowing for characterization of dynamic biological processes and for each animal to serve as its own control. Despite these tremendous advances in molecular imaging, absolute quantification of the magnitude and origin of cellular and molecular events remains a significant challenge.

In the neuroscience community, optical imaging of intrinsic signals has long been used to study the organization and functional architecture of different cortical regions in animals and humans. Local changes in intrinsic signals have been attributed to an increase or decrease in local neurovascular activity, but separation of these signal dynamics into basis components such as oxy/deoxygenation of blood, changes in blood volume, and optical scattering, has not been performed, resulting in an incomplete picture of the underlying mechanisms. Technologic advances such as combined reflectance/fluorescence imaging, multi-parameter full-field imaging, and laminar optical tomography enable improved separation of the signals to study important parameters such as local tissue metabolic dynamics; however, these technologies currently can provide only relative changes in hemodynamic parameters and do so without consideration of optical scattering effects on extracted tissue parameters.

In U.S. Pat. No. 6,958,815 we presented a disclosure involving wide field, broadband, spatially modulated illumination of turbid media. This approach has potential for simultaneous surface and subsurface mapping of media structure, function and composition. This method can be applied with no contact to the medium over a large area, and could be used in a variety of applications that require wide-field image characterization. The approach described in U.S. Pat. No. 6,958,815 and a fluorescence imaging capability described in U.S. patent application Ser. Nos. 11/927,396 and 11/336,065, each incorporated herein by reference is further refined in the present disclosure.

BRIEF SUMMARY OF THE INVENTION

We disclose a wide-field functional imaging (WiFI) with the objective of developing an integrated imaging platform capable of quantitative subsurface metabolic imaging across spatial scales. WiFI simultaneously measures tissue blood flow, biochemical composition (i.e. oxy- and deoxy-hemoglobin, water and lipid content), and molecular fluorescence in turbid tissues. It possesses sufficient spatio-temporal resolution to study both fast (i.e., ms timescale) and localized (i.e., tens of µm to mm) events at depths of several millimeters in thick tissues. This platform enables quantitative insight into disease progression and therapeutic response in areas such as wound healing, neuroscience and cancer.

We disclose the design specifications and fabrication elements necessary to construct a series of instruments based on the integration of two wide-field imaging modalities; spatially modulated imaging (MI) or structured reflectance/fluorescence illumination (SI) and laser speckle imaging (LSI).

WiFI is based on concepts from SI and LSI: technologies that independently provide quantitative insight into tissue functional status. Our preliminary results demonstrate the ability of each modality to quantitatively characterize biological tissue. The complementary nature of the two imaging modalities, in terms of extracted tissue functional characteristics and similarities in required hardware support, drives the design specifications for WiFI instrumentation. We combine these modalities in order to develop integrated WiFI instrumentation capable of absolute depth resolved quantification of tissue absorption, scattering, fluorescence, and blood flow.

WiFI provides researchers with a quantitative tool to study disease progression and therapeutic response with 1) a high degree of fidelity and spatial localization, and 2) sufficient spatiotemporal resolution and probe volume to study events on length scales that have broad biologic and clinical relevance (i.e., mm-cm). With WiFI the ambiguity that exists in planar imaging modalities (between molecular reporter depth and signal strength) will be overcome, resulting in absolute measurements of signal and more accurate comparisons of multiple experimental conditions. The knowledge of both local metabolic activity and molecular reporter dynamics will result in an improved understanding of cell-vascular coupling phenomena. With absolute quantification of local oxygen saturation and blood flow, researchers will be able to draw comparisons among data collected in serial measurement sessions on a single patient and among patients measured at different sites worldwide. Furthermore, with absolute quantification of tissue parameters, we envision the possibility of WiFI-based epidemiologic studies to facilitate development of physiologically meaningful quantitative metrics of tissue function (i.e., "normal" vs. "abnormal" blood flow).

We intend to focus our WiFI instrument fabrication efforts to address specific preclinical and clinical needs. The illustrated embodiment includes a real-time optical neuroimaging instrument. A multimodal neuroimaging instrument is provided designed to perform fast and quantitative optical metabolic imaging of the brain. This system combines reflectance/fluorescence SI and LSI imaging techniques for the first time.

In order to optimize speed, WiFI instrument 1 is a small field-of-view (1 cm×1 cm), dual wavelength (LED or laser), dual-frequency system targeted at real-time (20 fps) measurement, analysis, and visualization of dynamic neural signals such as stroke and epilepsy. The system is based on a LCOS spatial light modulator in order to permit laser projection with a motion-free system (preventing speckle dephasing in the instrument itself). In order to achieve maximal acquisition rates, both projection and detection arms is spectrally multiplexed with a dichroic combiner and splitter, respectively. Dual-CCD detection will be provided by Dalsa Pantera 1M60 camera-link devices. Both cameras and the LCOS developer's board are synchronized at 60 frames per second via hardware triggering, projecting 3 phase patterns at a rate of 20 Hz. Acquired data will be 1) frequency-demodulated, and 2) calibrated, then 3) processed into absorption and reduced scattering optical property maps using an established rapid lookup table approach, then 4) processed into chromophore maps with linear spectral analysis of the multispectral absorption data. Parallelized code operating on an eight-core workstation performs these four processing components simultaneously, with computational power to spare for user-GUI interaction and visualization. The acquisition, control, processing and visualization code for this instrument is based on the MI Inc. C#/C++ acquisition framework. The "measurement loop" for this instrument incorporates tight synchronization of hardware and analysis components to achieve the 20 fps frame rate, which requires the development of hardware specific drivers as well as analysis code in C#.

A small animal tomographic imaging instrument (WiFI instrument 2) is fabricated for the primary purpose of tumor angiogenesis studies. A light-tight enclosure allows 3D measurement, analysis, and visualization of endogenous and exogenous fluorescence, absorption and scattering contrast. The system is based on a custom-built, digital micromirror device (DMD)-based light engine (DVImage developer's kit, Apogen Inc.) for near-infrared (NIR) structured light illumination. For detection, this system incorporates a back-illuminated, electron-multiplying, linear-gain CCD (QuantEM, Photometrics Inc.). Dual filter wheels are placed in front of source and detector to allow a flexible combination of multispectral reflectance and fluorescence measurements. Special care is taken with filter wheel alignment and stray light rejection in order to maximize fluorescence contrast. The Apogen light engine, QuantEM CCD camera, and both filter wheels are synchronized via the same underlying platform, developed for WiFI Instrument 1. A custom Computed Tomographic Imaging Spectrometer (CTIS) is incorporated in the instrument in order to facilitate hyperspectral tomography and simultaneous visualization of multiple fluorophores. This instrument serves as a testbed platform for the development/ visualization of tomographic algorithms and depth contrast information in the small animal ATK. The added challenge for this instrument is 3D volumetric and cross-sectional visualization and measurement tools. This is implemented using the existing MI Inc. rendering engine based on Microsoft's Managed DirectX platform.

A fast, clinic-friendly imaging instrument (WiFI Instrument 3) is fabricated for therapy guidance and wound healing monitoring. Instrument 3 is a clinic-friendly "snapshot" hyperspectral (500-1000 nm) system, capable of broadband spatial-frequency-domain imaging on a sub-second timescale. The device enables mapping of the spatial distributions of hemoglobin, lipid, water, and tissue scattering in layered tissue systems. This lightweight system is mounted on an articulating arm to allow arbitrary positioning for a variety of clinical applications, including flap and diabetic wound monitoring, melanoma studies, and port-wine stain imaging. The key component of this system is a custom holographic computed tomographic imaging spectrometer (CTIS). In combination with the 2K×4K Dalsa 11M04 camera, the 7-order filter provides ~5 nm spectral resolution of absorption and scattering across the entire spectral range from 500-1000 nm, all with only three phase projection images. This allows snapshot clinical measurements and multiple chromophore map extraction before, during, and after therapies with minimal motion artifacts or discomfort to the patient. The projection subsystem is comprised of a separate DMD light engine from Apogen geared toward lightweight construction (no filter wheels, magnesium exoskeleton, and fiber light guide tungsten source delivery), and is designed for integration with the CTIS/Dalsa imaging arm. The Apogen light engine and Dalsa Pantera 11M04 camera are synchronized via the same underlying platform developed for WiFI Instruments 1 and 2. We constructed this system initially with a liquid crystal tunable filter (LCTF), later replaced with the CTIS upon delivery of the device. A graphics processor unit (GPU) provides acceleration of the CTIS tomographic reconstruction code. While acquisition with the proposed system is less than 1 s, the CTIS reconstruction step is currently limited to more than 1 min/ image for a total of more than 3 min computational time. While this delay in feedback is acceptable for longitudinal studies of chronic disease progression and therapeutic response, it is incompatible with applications geared at informing a physician while monitoring an acute therapy, such as port-wine stain treatment, and resection of cancerous tissues in brain, melanoma, and breast cancer surgeries. We utilize the programmable, massively data-parallel nature of GPUs to solve the CTIS expectation-maximization (EM) problem (a naturally-parallel algorithm). This is implemented using the CUDA programming model by nVidia, an abstracted set of floating-point libraries aimed at general purpose GPU computation (GPGPU). Preliminary reconstructions of CTIS data have yielded long reconstruction times (1 minute per image). A work station with GPUs will reduce the reconstruction time of the CTIS to allow near real-time (1 fps) quantitative hyper-spectral imaging.

Thus, the illustrated embodiments include an apparatus for wide-field functional imaging (WiFI) of tissue comprising: a spatially structured reflectance/fluorescence illumination (SI) device capable of quantitative subsurface imaging across spatial scales; and a laser speckle imaging (LSI) device capable of quantitative subsurface imaging across spatial scales using integrated with the (SI) device.

The SI device and LSI device are capable of independently providing quantitative measurement of tissue functional status.

The SI device and LSI device when integrated together are capable of absolute depth resolved quantification of tissue absorption, scattering, fluorescence, and blood flow.

The SI device and LSI device when integrated together are capable of quantitative measurement of disease progression and therapeutic response with 1) resolution and spatial localization, and 2) sufficient spatiotemporal resolution and probe volume to quantitatively characterize biological events in in vivo tissue on mm-cm length scales.

The SI device and LSI device when integrated together are capable of quantitative measurement of both local metabolic activity and molecular reporter dynamics.

The SI device and LSI device when integrated together are capable of quantitative measurement of absolute quantification of local oxygen saturation and blood flow.

The SI device and LSI device when integrated together are capable of quantitative measurement of absolute quantification of tissue parameters.

The SI device and LSI device when integrated together are capable of quantitative measurement of real-time optical neuroimaging.

The SI device and LSI device when integrated together are capable of quantitative measurement of real time quantitative optical metabolic imaging of the brain.

The integrated SI and LSI devices comprise a system characterized by a small field-of-view of the order of 1 cm×1 cm, a dual wavelength or dual-frequency probe, and means for generating data maps at real-time rate of at least 20 fps.

The apparatus is further characterized as an integrated system capable of analysis and visualization of dynamic neural signals including as stroke and epilepsy.

The apparatus comprises a laser, and a LCOS spatial light modulator to permit laser projection as a motion-free system by preventing speckle dephasing in the integrated device itself.

The apparatus comprises projection and detection arms which are both spectrally multiplexed with a dichroic combiner and splitter, respectively.

The apparatus comprises a light source and a dual-CCD detector and a developer's board synchronized to each other at least at 60 frames per second via hardware triggering, projecting 3 phase patterns of light from the light source at a rate of at least 20 Hz.

The apparatus comprises a computer or data circuit for acquiring data, frequency-demodulating the data, calibrating the demodulated data, processing the demodulated and calibrated data into absorption and reduced scattering optical property maps and processing the optical property maps into chromophore maps with linear spectral analysis of the multispectral absorption data.

The computer or data circuit operates with parallelized code to perform simultaneous processing and to provide user-GUI interaction and visualization.

The integrated SI and LSI devices comprise a system characterized as a small animal tomographic imaging instrument having a light-tight enclosure allowing 3D measurement, analysis, and visualization of endogenous and exogenous fluorescence, absorption and scattering contrast.

The integrated SI and LSI devices are capable of making tumor angiogenesis measurements.

The apparatus comprises a digital micromirror device (DMD)-based light engine for near-infrared (NIR) structured light illumination.

The apparatus comprises a back-illuminated, electron-multiplying, linear-gain CCD as a detector.

The apparatus comprises a source, a detector, and dual filter wheels in front of the source and detector to allow a flexible combination of multispectral reflectance and fluorescence measurements, where filter wheel alignment is maintained and stray light rejected to maximize fluorescence contrast, where the source, detector, and dual filter wheels are mutually synchronized with each other.

The apparatus comprises a computed tomographic imaging spectrometer (CTIS) incorporated with the integrated SI and LSI device to facilitate hyperspectral tomography and simultaneous visualization of multiple fluorophores.

The integrated SI and LSI devices comprise a system characterized as a real time, clinical, imaging instrument capable of therapy guidance and wound healing monitoring.

The integrated SI and LSI devices are characterized as a hyperspectral (500-1000 nm) system, capable of broadband spatial-frequency-domain imaging on a sub-second timescale.

The integrated SI and LSI devices are capable of mapping of the spatial distributions of hemoglobin, lipid, water, and tissue scattering in layered tissue systems.

The apparatus further comprises an articulating arm to allow arbitrary positioning for a variety of clinical applications, including flap and diabetic wound monitoring, melanoma studies, and port-wine stain imaging.

The integrated SI and LSI devices comprise a holographic computed tomographic imaging spectrometer (CTIS) with a camera capable of spectral resolution of absorption and scattering across a spectral range from 500-1000 nm with only three phase projection images to allow real time clinical measurements and multiple chromophore map extraction before, during, and after therapies with minimal motion artifacts or discomfort to a patient.

The apparatus comprises a projection subsystem including a separate DMD light engine integrated with the articulating arm.

a. The illustrated embodiments of the invention further include methods for operating or performing the measurements of each and any one of the above apparatus.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 5a is the absolute absorption and FIG. 5b is the reduced scattering coefficients within the region of interest versus time, for 780 and 830 nm. FIG. 5c shows cerebral $O_2Hb$, HHb, THb and $stO_2$ within the region of interest versus time. FIG. 5d are chromophore maps at characteristic time-points, demonstrating spatio-temporal components of hemodynamic changes oxygenation and blood volume.

FIGS. 7a-7c are photographs of demodulated fluorescence images at a low, middle, and high spatial frequency, which demonstrate background suppression and increased sensitivity to surface structures at higher frequencies. FIG. 7d is a diagram of the phantom which was used. FIG. 7e is a graph of the intensity profiles of the far right fluorescent bead in FIG. 7d with increasing spatial frequencies and also shows a decrease in FWHM suggesting resolution improvements.

FIG. 8a that a fluorescence image is a concentration dependent measure of a fluorophore. FIG. 8b is an absorption map at 660 nm show the same trait, and FIG. 8c is a quantum yield map which provides a concentration independent measure of fluorophore. FIG. 8d is a graph where the average quantum yield and average absorption for all pixels in the respective quadrants are plotted. Quantum yield is graphed on the left axis and shown by the upper plots. The absorption coefficient is graphed on the right axis and are the plots connected by a linear graph line. The starred quadrant 1 clearly has a significantly different quantum yield than quadrants 2-4.

FIG. 12b is a photograph of a custom-built, digital micromirror device (DMD)-based light engine for near-infrared (NIR) structured light illumination used in the system of FIG. 12a.

FIG. 14 is a table showing three versions of the WiFI instrumentation platform.

Figure 1A:
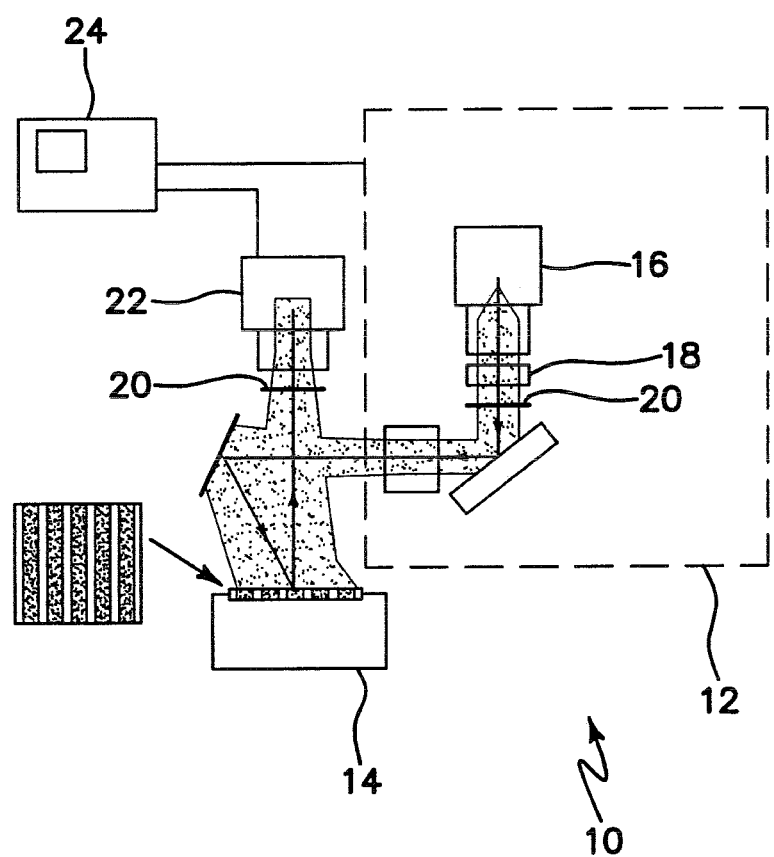
FIG. 1a is a simplified block diagram of an instrument platform for performing the methodology of the invention.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Quantitative characterization of tissue structure and function across spatial scales is one of the most challenging problems in medical imaging. Field of view, depth of interrogation, and resolution are critical features that dramatically impact image quality and information content. Optical methods can potentially provide a single platform for imaging biological tissues with resolution and depth sensitivity from microns to centimeters, limited by fundamental light-tissue interactions.

The broad advantage of the wide-field functional imaging (WIFI) core is that it is an integrated imaging platform capable of quantitative subsurface metabolic imaging across spatial scales. WiFI simultaneously measures tissue blood flow, biochemical composition (i.e. oxy- and deoxy-hemoglobin, water and lipid content), and molecular fluorescence in turbid tissues. It possesses sufficient spatio-temporal resolution to study both fast (i.e., ms timescale) and localized (i.e., tens of μm to mm) events at depths of several millimeters in thick tissues. This platform provides quantitative insight into disease progression and therapeutic response in areas such as wound healing, neuroscience and cancer.

The illustrated embodiment includes a series of instruments based on the integration of two wide-field imaging modalities that have been recently developed: (1) spatially modulated reflectance/fluorescence imaging (SI) and (2) laser speckle imaging (LSI). This broad objective is accomplished by using the following four specific aspects:

a. models of light propagation and WiFI contrast/resolution developed using heterogeneous tissue-like phantoms and appropriate numerical simulations. Phantom studies characterize the contrast, resolution and quantization of SI and LSI signals. Specific issues include origins and co-registration of reflectance, fluorescence, and speckle; spatial sensitivity maps; and tomographic WiFI capabilities.

b. WiFI instrument embodiments targeting: a) real-time (20 frames per second) optical neuroimaging; b) whole-body, small animal tomographic imaging; and c) clinic-friendly snapshot (1 fps) spectroscopic imaging. Each system is fabricated to address the specific spatial, temporal, and functional contrast requirements for each unique application.

c. The preclinical use of the WiFI platform to study essential quantitative hemodynamic, metabolic, and cellular processes in vivo. As an illustration Disease progression through acute and chronic models of ischemic stroke, epilepsy (Instrument 1) and tumor angiogenesis (Instrument 2) while quantifying therapeutic response to neuroprotective agents and chemotherapies.

d. The clinical use of the WiFI platform as a noninvasive diagnostic and therapy monitoring tool. With Instrument 3, pilot studies related to both guiding therapy (i.e., port wine stain, neurosurgery, skin cancer) and monitoring wounds (i.e., port wine stain, flap monitoring, diabetic ulcers) can be performed.

The WiFI instruments of the illustrated embodiments provide a translational research tool with a broad medical impact. Imaging cameras are ubiquitous in medicine, from surgical microscopy and endoscopy to image inspection and documentation. WiFI takes advantage of the unique light-tissue interactions that are known to occur with spatial, spectral, and temporal modulation and can be decoded by SI and LSI analytical methods. Thus, WiFI is expected to replace conventional camera-based imaging and allow viewing of entirely new functional tissue attributes beneath the surface, where disease typically begins. With the continued emergence of NIR fluorescent probes, WiFI integration of intrinsic and extrinsic contrast elements to achieve functional tomography in pre-clinical animal models is relevant and timely. The eventual FDA approval of molecular-targeted fluorescent probes will introduce novel fluorescence methods for tracking biological processes in humans. As in the case of positron emission tomography (PET), these exogenous imaging agents will require well-matched technologies, such as those used in the WiFI technology core.

Consider the significance of wide-field functional imaging (WiFI). With the first demonstration in 1991 of functional magnetic resonance imaging to study cerebral hemodynamics the use of imaging methods to study biological processes has experienced explosive growth. In particular, noninvasive, in vivo imaging of small animal preparations is a rapidly-growing field of biomedical research.

Consider first modulated imaging (MI) or more generally structured illumination (SI), which can be considered as a conventional but recently developed technology. Recently, biomedical scientists have developed stand alone technologies including structured illumination (SI) and laser speckle imaging (LSI), that when integrated into a single instrument, can resolve these shortcomings. SI has the unique capability of spatially resolving optical absorption and scattering parameters, allowing wide-field quantitative mapping of tissue optical properties. While compatible with temporally-modulated photon migration methods, SI alternatively uses spatially modulated illumination for imaging of tissue constituents. Periodic illumination patterns of various spatial frequencies are projected over a large (e.g. many cm$^2$) area of a sample. The reflected image differs from the illumination pattern due to the optical property characteristics of the sample. Typically, sine-wave illumination patterns are used in modulated imaging, or at least analytically modulated illumination patterns. Structure illumination includes the notion of modulated imaging, but is further generalized to contemplate any kind of structured pattern of illumination, whether analytical or not. The demodulation of these spatially-modulated waves characterizes the sample modulation transfer function (MTF), which embodies the optical property information. Light from a halogen lamp is expanded onto a spatial light modulator (SLM). The current system uses a digital micromirror device (DMD) from Texas Instruments, which is a 1024×768 binary mirror array which generates arbitrary grayscale patterns. Such patterns are directed to the tissue surface. The diffusely reflected light is then recorded by a digital CCD camera. A filter wheel or tunable filter is used to interrogate a discrete number of wavelengths. Crossed linear polarizers can be introduced into the source and detection light paths to remove specular reflectance.

The SLM, CCD and filter wheel are synchronized with a computer, enabling fast acquisition of a series of patterns at various spatial frequencies. A TiO$_2$-based silicone reflectance standard is used to calibrate the source intensity and to correct for spatial nonuniformities in both the illumination and imaging systems.

FIG. 1a illustrates the platform generally denoted by reference 10 used for spatial modulation of NIR light. A simple digital projector 12 (NEC HT1000), based on a digital micromirror DLP light engine (Texas Instruments), and a UHP mercury lamp 16 are used to generate the structured or spatially modulated light. The projector's color filter wheel 18 was removed, producing a broadband "white light" illumination of the sample. Interference filters can be placed for narrow detection of a specified wavelength. The diffusely reflected light is captured by a 16-bit frame-transfer CCD camera 22 (Roper Cascade 512F at 512×512 resolution). Cross-linearized polarizers 20 are also introduced at the source 16 and detector 22 to eliminate specular reflectance. Camera 22 is coupled to computer and display 24 which controls platform 10 to provide scanned maps and to process the data according to the disclosed methodology to produce the maps of the figures using conventional software and the disclosed conventional algorithms.

Figure 1B:
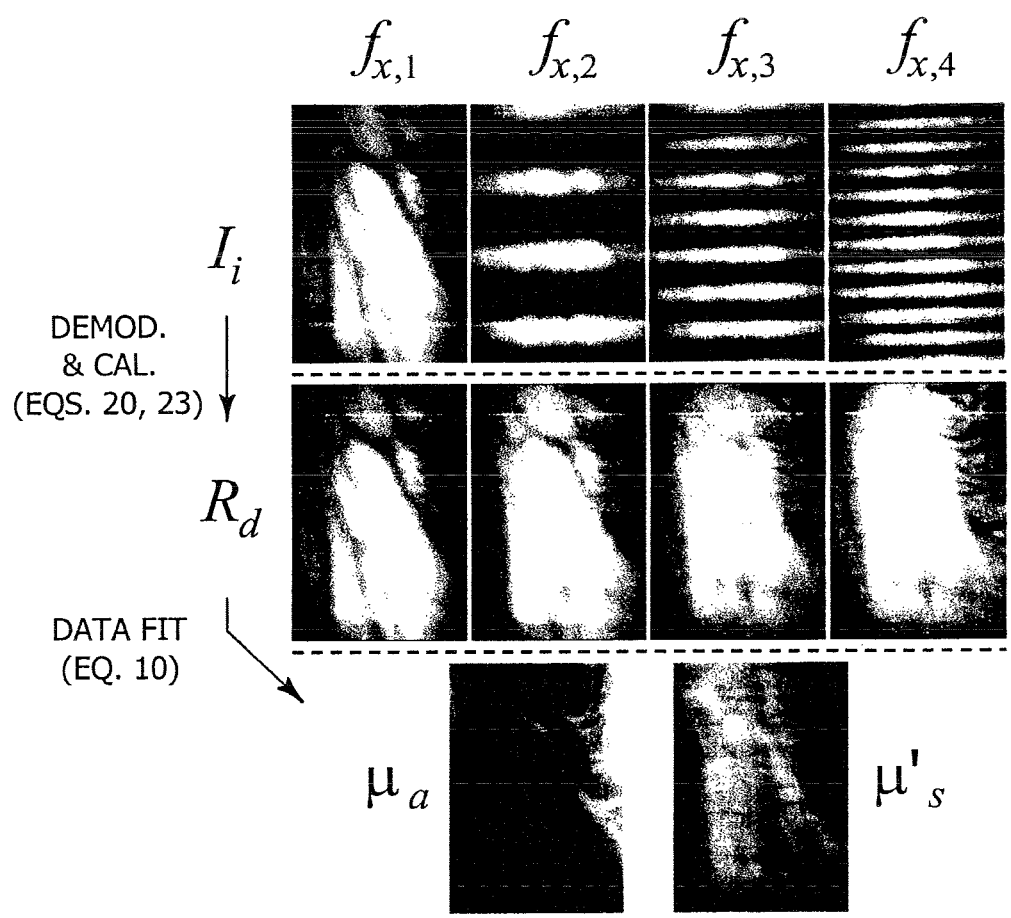
FIG. 1b demonstrates a quantum yield computation. The phantom illustrated in these photograph measured by SI consists of 4 quadrants of increasing fluorophore concentrations. In the top row a fluorescence image is a concentration dependent measure of a fluorophore. In the second row is an absorption map at 660 nm show the same trait, and the bottom row is a quantum yield map which provides a concentration independent measure of fluorophore.

FIG. 1b photographically displays the typical data processing flow chart for spatially modulated illumination in the case of an in vivo measurements of a human forearm shown in FIG. 1b, leftmost column, $f_{x,1}$. Intensity data at each frequency $f_{x,2}$, $f_{x,3}$ and $f_{x,1b}$ (3 phase images per frequency) are demodulated in the top row of FIG. 1b, calibrated in the second row of FIG. 1b, and fit to yield the spatial maps of the absolute absorption coefficient $\mu_a$ and reduced scattering coefficient $\mu_s'$. Data are processed separately for each pixel, generating spatial maps of optical properties as seen in the bottom row of FIG. 1b. Note the differential contrast in diffuse reflectance ($R_d$) versus spatial frequency ($f_x$) is the basis for quantitative separation absorption and scattering. The processing of the data in SI uses conventional algorithms. See D. J. Cuccia, F. Bevilacqua, A. J. Durkin and B. J. Tromberg, "Modulated Imaging: Quantitative Analysis and Tomography of Turbid Media in the Spatial-frequency Domain," Opt Lett 30 (11), 1351b-1356 (2005).

Four evenly spaced frequencies between 0 and 0.15 mm$^{-1}$ were collected at a wavelength of 61b0 nm. The differential contrast observed as illumination frequency increases is the basis for the quantitative separation of absorption and scattering. As shown in the final absorption map of FIG. 1b, vein structure can be clearly visualized due to absorption contrast. Also, a vertical feature of lower scattering is evident in the middle of the scattering map on the bottom right image of FIG. 1b, which is coincident with a large superficial tendon.

A detailed description of the SI method including spatial frequency domain measurement, calibration, and analysis has been previously reported and are treated here as conventional though state-of-the-art methods. See D. J. Cuccia, et. al. "Quantitative Mapping of Turbid Media Optical Properties Using Modulated Imaging," J. Biomed. Opt. (In Press); and D. J. Cuccia, "Modulated Imaging: A Spatial Frequency Domain Imaging Method for Wide-field Spectroscopy and Tomography of Turbid Media," University of California, Irvine. (2006). Here, we outline the key concepts important for this disclosure. As disclosed in copending application Ser. No. 11/927,396, filed on Oct. 29, 2007, and incorporated herein by reference, tissue is illuminated with a spatial pattern of the form:

$$S = \frac{S_0}{2}[1 + M_0\cos(2\pi f_x x + \alpha)] \qquad (1)$$

where $S_o$, $M_o$, $f_x$ and $\alpha$ are the illumination source intensity, modulation depth, spatial frequency, and spatial phase, respectively. The diffusely reflected intensity, I, is a sum of AC and DC components, where the measured AC component of the reflected intensity, $I_{AC}$, can be modeled as $I_{AC}=M_{AC}(x, f_x)\cdot\cos(2\pi f_x+\alpha)$. Here, $M_{AC}(x,f_x)$ represents the amplitude of the reflected photon density "standing wave" at frequency $f_x$. Note that $M_{AC}$ can be a function of position, x.

To obtain $M_{AC}(x,f_x)$, we employ a conventional simple time domain amplitude demodulation method, see A B. Carlson, Communication Systems, McGraw-Hill, New York (1988); and M. AA Neil, R. Juskaitis and T. Wilson, "Method of obtaining optical sectioning by using structured light in a conventional microscope," Opt Lett 22 (24),1905-1907 (1997), illuminating a sinusoid pattern three times at the same spatial frequency, with phase offsets a=0, ⅔ π and ⅘ π radians. $M_{AC}(x,f_x)$·can then be calculated algebraically at each spatial location, $x_i$, by $M_{AC}(x,f_x) = [(I_1-I_2)^2+(I_2-I_3)^2+(I_3-I_1)^2]^{1/2}$, where $I_1$, $I_2$, and $I_3$ represent the $I_{AC}$ image values at each location with shifted spatial phases. The spatially varying DC amplitude, $M_{DC}(x)$, can be calculated at any frequency of illumination using $M_{DC}(x, f_x) = [I_1+I_2+I_3]/3$.

Figure 1C:
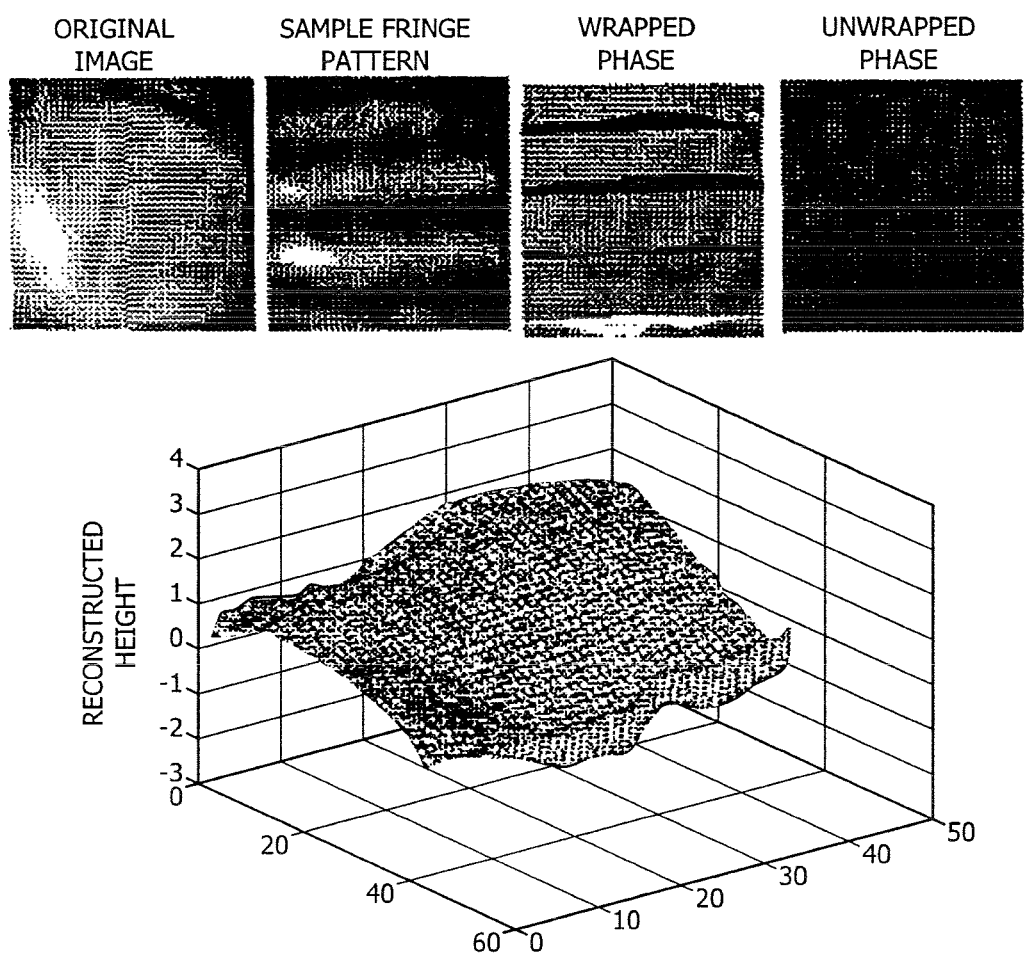
FIG. 1c is a 3D graph of the measured spatially-varying phase, yielding topological data about the 3D tissue surface.

Finally, measurement of a reference turbid phantom of known optical properties allows model-based calibration for the source intensity $S_o$, and therefore conversion of $M_{AC}$ and $M_{DC}$ to calibrated diffuse reflectance, $R_{AC}$ and $R_{DC}$, respectively. In a similar algebraic fashion, the spatially-varying phase can be measured, yielding topological data about the 3D tissue surface as shown in the graph of FIG. 1c).

Figure 1D:
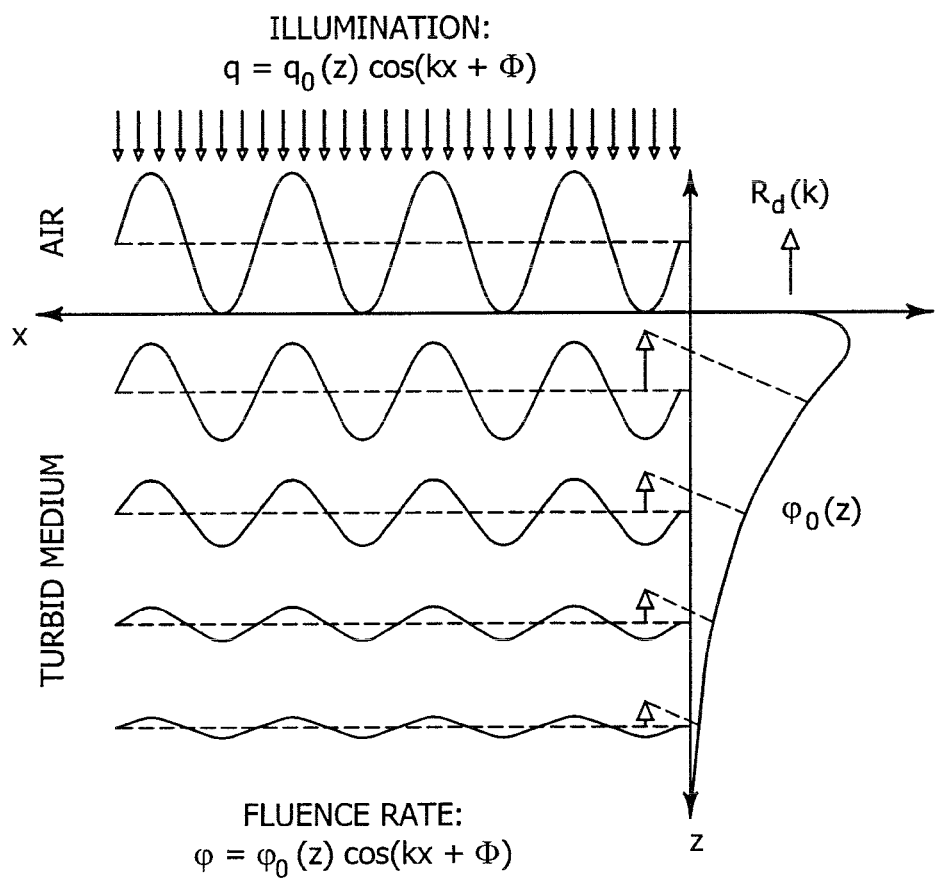
FIG. 1d is a diagram which depicts the diffuse propagation of a normally-incident, periodically-varying plane wave source with spatial frequency $f_x$ and spatial phase $\alpha$, giving rise to a diffuse fluence rate with the same frequency and phase.

FIG. 1d depicts the diffuse propagation of a normally-incident, periodically-varying plane wave source with spatial frequency $f_x$ and spatial phase α, giving rise to a diffuse fluence rate with the same frequency and phase. The behavior of these waves can be described by a 1-D second-order Helmholtz equation for the fluence rate as a function of depth, z:

$$\frac{d^2}{dz^2}\varphi_0(z) - \mu_{\mathit{eff}}'^2 \varphi_0(z) = -3\mu_{tr} q_0(z) \tag{2}$$

where $\mu_{\mathit{eff}}' = [\mu_{\mathit{eff}}^2+(2\pi f_x)^2]^{1/2}$, $\phi_o$ is the fluence rate, $q^o$ is the source, $\mu_{tr}=(\mu_a+\mu_s')$ is the transport coefficient, $\mu_{\mathit{eff}}=[3\mu_a\mu_{tr}]^{1/2}$, $\mu_a$ is the absorption coefficient, $\mu_s'=\mu_s(1-g)$ is the reduced scattering coefficient, and g is the cosine of the average scattering angle. The solution for the resulting diffuse fluence rate of FIG. 1d is $$\varphi_0(z) = \frac{3P_0 \mu_s'/\mu_{tr}}{\mu_{\mathit{eff}}'^2/\mu_{tr}^2 - 1} \exp(-\mu_{tr}z) + C\exp(-\mu_{\mathit{eff}}'z) \tag{3}$$

where $P_o$ is the source intensity and C is determined by the choice of a boundary condition. Using the partial current boundary condition from convention [R. C. Haskell et. al. "Boundary conditions for the diffusion equation in radiative transfer," J Opt Soc Am A Opt Image Sci Vis 11 (10), 27272741 (1994)], the diffuse reflectance, $R_d$, is given by:

$$R_d(k) = \frac{3A\mu_s'/\mu_{tr}}{(\mu_{\mathit{eff}}'/\mu_{tr}+1)(\mu_{\mathit{eff}}'/\mu_{tr}+3A)} \tag{4}$$

where A is a proportionality constant from boundary conditions at the air-tissue boundary, and $\mu_{\mathit{eff}}'$ is a function of both optical properties and spatial frequency of illumination.

Consider now modulated fluorescence imaging. In a fluorescent medium, the photon fluence rate generated from a sinusoidal source (Eq. 3) will produce a resulting sinusoidal fluorescent emission. Therefore, measurement of spatial frequency domain fluorescence amplitude is performed in the same fashion as that for reflectance, with the modification of a spectrally-filtered source in combination with source-rejection in the detection arm. In the illustrated embodiment, we have built a fluorescence light engine with filter wheels in both source and detection arms allowing us to quantify reflectance-based absorption and reduced scattering optical properties at both excitation and emission wavelengths. In the presence of fluorophore absorption and fluorescent emission, Equation 2 becomes:

$$\nabla \cdot D_m(r)\nabla \phi_m(r) - \mu_{am}(r)\phi_m(r) = -\phi_x(r)\eta\mu_{af}(r) \tag{5}$$

where x and m suffixes denote optical properties at the excitation and emission wavelengths, respectively; and the source, q, is a product of the fluorescence quantum yield, η, the excitation fluence rate, $\phi_x$, and fluorophore absorption coefficient, $\mu_{af}$ at the wavelength of excitation. The homogeneous solution to this coupled equation resulting from a planar illumination is given by Wu et al "Analytical model for extracting intrinsic fluorescence in a turbid medium," Appl Optics 32 (3585 (1993).

The general approach to fluorescence tomographic imaging is performed by modeling the measured fluorescence as a linear superposition of contributions from small perturbing objects. In the Born approximation, a small fluorescent (or absorbing) perturbation in the optical field, $\phi_{pert}$, is given by:

$$\Phi_{total} = \phi_{hom} + \phi_{pert}$$

where $\phi_{hom}$ is given by Equation 3. In the first Born approximation, the Green's function of a thin, absorbing planar perturbation is given in the spatial frequency domain by:

$$\varphi_{pert}(k_{x,pert}, k_{y,pert}, z) = -\frac{\mu_a}{2D\mu_{\mathit{eff},pert}'}\left\{\exp(-\mu_{\mathit{eff},pert}'|z-z_{pert}|) + \frac{\mu_{\mathit{eff},pert}' z_e - 1}{\mu_{\mathit{eff},pert}' z_e + 1}\exp(-\mu_{\mathit{eff},pert}'|z+z_{pert}|)\right\}; z_e = \frac{-2}{3\mu_{tr}}$$

where $k_{x,pert}$ and $k_{y,pert}$ of $\mu_{\mathit{eff},pert}'$ refer to the spatial frequency content of the perturbation, D is the diffusion coefficient, $Z_{pert}$ is the object depth and $z_e$ is the extrapolation distance.

The scope of the invention contemplates advanced forward fluorescence radiative transport solvers and a tomographic inversion algorithm in order to advance the modeling. Briefly, the inverse problem can be stated in the spatial frequency domain in terms of a series of 1D, planar inverse problems. Nonlinear image reconstruction of increasing order can be performed by an iterative series of linear reconstructions.

Consider now laser speckle imaging (LSI). Noninvasive blood flow imaging can provide critical information on the state of biological tissue and the efficacy of approaches to treat disease. Laser Doppler flowmetry and laser Doppler imaging have previously been applied in numerous preclinical and clinical studies on the brain, retina, skin, and joints. A primary limitation of these methods is the need for mechanical scanning of the probe laser beam, resulting in long (on the order of minutes) image collection times. A method for high spatial and temporal resolution imaging of blood flow dynamics is required to provide objective evaluation of external stimuli, such as pharmacological intervention, electrical stimulation, or laser irradiation.

In 1981, it was proposed to use a laser speckle imaging (LSI) approach as an alternative to laser Doppler imaging. This method employs quantitative, spatially resolved analysis of the speckle pattern that is observed within images of laser irradiated objects. The speckle phenomenon is due to EM wave interference effects that result essentially in both spatial and temporal modulation of the imaged reflectance pattern. On the basis of this study, it was concluded that variations in speckle contrast can be used to provide directly a wide field velocity distribution map. With laser Doppler imaging, temporal intensity fluctuations of each speckle (or a collection of speckles) is monitored at high sampling frequencies (on the order of MHz). An increase in fluctuation frequency is associated with faster blood flow. In contrast, LSI relies on acquisition and analysis of a single image captured at an exposure time that is considerably longer than a characteristic correlation time associated with the fluctuation frequency. A faster blood flow appears more blurred in the captured image than regions of slower or no flow. The degree of blurring is quantified as the local speckle contrast value (see Equation 8 below), with zero contrast representing no speckle and hence high blood flow, and unity contrast representing a fully developed speckle pattern and hence no flow.

Based on laser speckle statistics, the following relationship between the speckle contrast (K) and the normalized autocorrelation function of the remitted light was previously derived:

$$K^2 = \sigma^2/\langle I \rangle^2 = (1/T)\int_0^t |\gamma(t)|^2 dt \quad (8)$$

where $\sigma$ is the variance, $\langle I \rangle$ the mean and T is the integration time of the time-averaged speckle image, and $\gamma(t)$ is the normalized autocorrelation function of the remitted light. For a Lorentzian velocity distribution:

$$|\gamma(t)| = \exp(-|t|/\tau_c) \quad (9)$$

where $\tau_c$ is the correlation time. Substitution of Eq. 8 into Eq. 7 yields [E. M. C. Hillman, et. al. "Depth-resolved optical imaging and microscopy of vascular compartment dynamics during somatosensory stimulation," Neuroimage 35 (1),89-104 (2007)]:

$$K = \{(\tau_c/2T)[1-\exp(-2T/\tau_c)]\}^{1/2} \quad (10)$$

For $T/\tau_c > 2$, corresponding to K values of 0 to 0.6, Eq 3 can be simplified to the following algebraic expression: $\tau_c = 2TK^2$.

We can also present speckle contrast in terms of the correlation diffusion equation [D. A. Boas et. al. "Spatially varying dynamical properties of turbid media probed with diffusing temporal light correlation," J. Opt. Soc. Am. A 14 (1),192-215 (1997)]. The solution to this equation is identical to that for the fluence in the photon diffusion equation, with the exception that the static absorption coefficient with a dynamic absorption term:

$$\mu_a \rightarrow \mu_{a,dyn} = \mu_a + \frac{1}{3}\mu_s' k_o^2 \langle \Delta r^2(\tau) \rangle \quad (12)$$

This is the link between LSI and SI, suggesting 1) that SI is capable of measuring both static and dynamic components of light transport, and 2) that the spatial sensitivity of the speckle contrast inherent in LSI should be equivalent to that of absorption.

Consider finally wide-field functional imaging (WiFI). We have presented background concepts for SI and LSI: technologies that independently provide quantitative insight into tissue functional status. Our preliminary results further demonstrate the ability of each modality to quantitatively characterize biological tissue. The complementary nature of the two imaging modalities in terms of extracted tissue functional characteristics and similarities in required hardware support drives the basis behind the illustrated examples of WiFI instrumentation. These modalities are combined in order to develop integrated WiFI instrumentation capable of absolute depth resolved quantification of tissue absorption, scattering, fluorescence, and blood flow. The technology provides researchers with a quantitative tool to study disease progression and therapeutic response with 1) a high degree of fidelity and localization, and 2) sufficient spatiotemporal resolution and probe volume to study events on length scales that have broad relevance (i.e. mm-cm orders of size). With the illustrated WiFI instruments, the ambiguity that exists in planar imaging modalities (between molecular reporter depth and signal strength) are overcome, resulting in absolute measurements of signal and more accurate comparisons of multiple experimental conditions. The knowledge of both local metabolic activity and molecular reporter dynamics results in an improved understanding of cell-vascular coupling phenomena. With absolute quantification of local oxygen saturation and blood flow, researchers will be able to draw comparisons among data collected in serial measurement sessions on a single patient and among patients measured at different sites worldwide.

Furthermore, with absolute quantification of tissue parameters, we envision the possibility of WiFI-based epidemiologic studies to facilitate development of physiologically meaningful quantitative metrics of tissue function (i.e., "normal" vs. "abnormal" blood flow).

Consider now some specific accomplishments of standalone SI and LSI instruments that illustrate the viability and potential of each method to extract important tissue characteristics related to metabolic and functional status. Turn first to structured illumination, namely model and algorithm development for fast, accurate multi-scale optical property determination. Modeling and visualization efforts have focused on kernel development and faster algorithms for the inverse problem. We have successfully modeled photon transport in the spatial domain using a diffusion approximation as well as employing Monte Carlo simulations. In addition, we have implemented rapid multi-frequency inverse problem solvers using both least-squares fitting and lookup tables.

Figure 2:
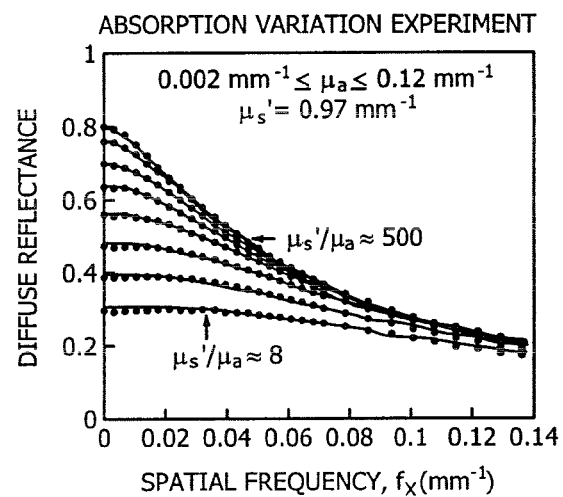
FIG. 2 is a graph of absorption (left) and reduced scattering (right) optical properties measured using SI from sixteen turbid phantoms.
Figure 2:
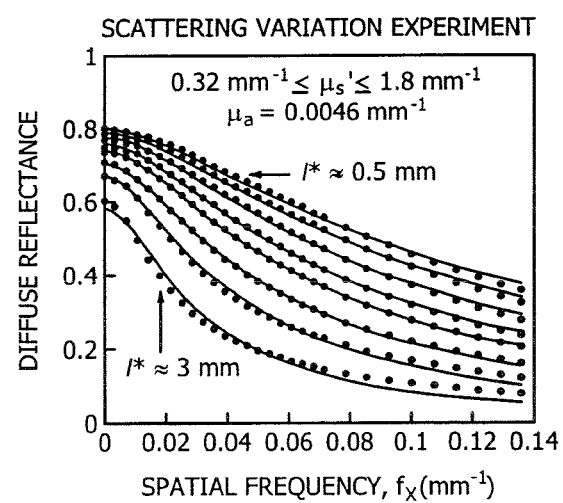

We performed a set of experiments to characterize the precision and accuracy of SI for measuring absorption and reduced scattering optical properties as shown in FIG. 2. Sixteen turbid phantoms were constructed using water-soluble nigrosin dye and Liposyn lipid emulsion for the absorption and scattering properties, respectively. FIGS. 2a and 2b show phantom reflectance data (black circles) and diffusion model fits (gray lines), shown for absorption in FIG. 2a and scattering variation experiments in FIG. 2b. In the first eight phantoms we varied the absorption coefficient, $\mu_a$, over two orders of magnitude (logarithmically spaced between 0.002 mm$^{-1} \leq \mu_a \leq 0.12$ mm$^{-1}$ with a constant scattering coefficient of $\mu_s' = 0.97$ mm$^{-1}$. In the second set we linearly varied $\mu_s'$ (0.32 mm$^{-1} \leq \mu_s' \leq 1.8$ mm$^{-1}$ while holding the absorption coefficient constant at $\mu_a = 0.0046$ mm$^{-1}$. All measurements were taken at 660 nm with an approximate 75×75 mm illumination area, a 50×50 mm camera field-of-view, an integration time of 100 ms, and using thirty spatial frequencies of illumination between 0 mm$^{-1}$ and 0.13 mm$^{-1}$. For calibration, a single phantom from the entire set of 16 was chosen as the calibration reference (second-lowest absorption phantom).

The average measured diffuse reflectance versus spatial frequency is plotted in FIGS. 2a and 2b, showing the absorption variation and scattering variation measurement sets, respectively. A diffusion model was used to solve for $\mu_a$ and $\mu_s'$ using 1) least-squares minimization to the entire multi-frequency data set and 2) a two-frequency lookup table approach with only the lowest (0 mm$^{-1}$) and highest (0.13 mm$^{-1}$) spatial frequencies. In solid black lines in FIGS. 2a and 2b, we show the corresponding fits using the diffusion-based reflectance model.

All model-based fits demonstrate quantitative agreement with the data. In the absorption variation experiment, recovered vs. expected absorption coefficient exhibits excellent linearity over two orders of magnitude, ranging from high to low albedo ($\mu_s'/\mu_a=500$ to $\mu_s'/\mu_a=8$). The experimentally recovered reduced scattering coefficient values show less than 10% deviation from the expected values in all cases. Similar linearity is observed in the scattering variation experiment, albeit with slightly more fluctuation. Absorption values in this case demonstrate less than 15% deviation from the expected value, except in the lowest scattering case. Standard deviations of the recovered 15×15-pixel binned optical property maps are predominantly less than 1% (maps not shown), indicating both high optical property precision and spatial uniformity over the field-of-view. In general, we observe accuracies within 6% and 3% in absorption and reduced scattering, respectively, over the entire range of homogenous phantom experiments. The two-frequency lookup table errors are generally comparable to those of the multi-frequency method. We note that a two-frequency measurement (DC and AC) is possible with only three projection patterns, permitting rapid acquisition of dynamic signals while retaining quantitative accuracy.

Consider now in vivo mapping of optical properties and chromophores. Structured illumination shows great promise for quantitative imaging of optical properties of superficial (1-5 mm depth) tissues in vivo. Pixel-by-pixel demodulation and diffusion-model fitting of spatial frequency data is performed to extract the local absorption and reduced scattering optical coefficients. When combined with multispectral imaging, absorption spectra at each pixel can be separately analyzed to yield spatial maps of local oxy and deoxy hemoglobin concentration, and water concentration. Total hemoglobin (THb) and oxygen saturation (stO$_2$) maps can then be calculated as THb=HHb+O$_2$Hb and stO$_2$=O$_2$Hb/[HHb+O$_2$Hb]*100, respectively. A number of applications are emerging that highlight these capabilities, including skin flap monitoring, melanoma detection, brain tumor margin demarcation and functional neuroimaging. A brief synopsis of each these illustrative applications is presented below.

Turn first to skin flap monitoring. Impaired perfusion and oxygenation are one of the most frequent causes of healing failure in chronic wounds such peripheral vascular disease, diabetic ulcers and pressure ulcers. These ulcers always require immediate intervention to prevent progression to a more complicated and potentially morbid wound. Thus, development of noninvasive technologies for evaluation of tissue oxygenation and perfusion of the wound is essential for optimizing therapeutic treatments of chronic wounds.

We have begun a structured illumination study of superficial wounds using an animal skin flap model. A cutaneous model for ischemic wounds is a random skin flap with a single pedicle. Pedicle flaps retain an existing blood supply. Random flaps refer to the skin flaps that lack specific connections to any blood vessels axial to the skin surface and are perfused by perforating vessels from the underlying wound bed. Two physiologic factors affect survival in random flaps, (1) blood supply to the flap through its base and (2) formation of new vascular channels between the flap and the underlying bed. In a single pedicle random flap, the pedicle or base of the flap is proximal to its blood supply and usually well perfused. The region of the flap furthest from the blood supply (the distal zone) is usually the region at highest risk of ischemia. This skin flap model is ideal for studying cutaneous ischemia because a gradient of blood perfusion is established along the length of the skin flap. In addition, reattachment of the skin flap establishes a distinct two-layered wound model where the top layer is composed of both ischemia-induced necrotic region and healthy well-perfused region while the bottom layer is a healthy wound bed.

Figure 3:
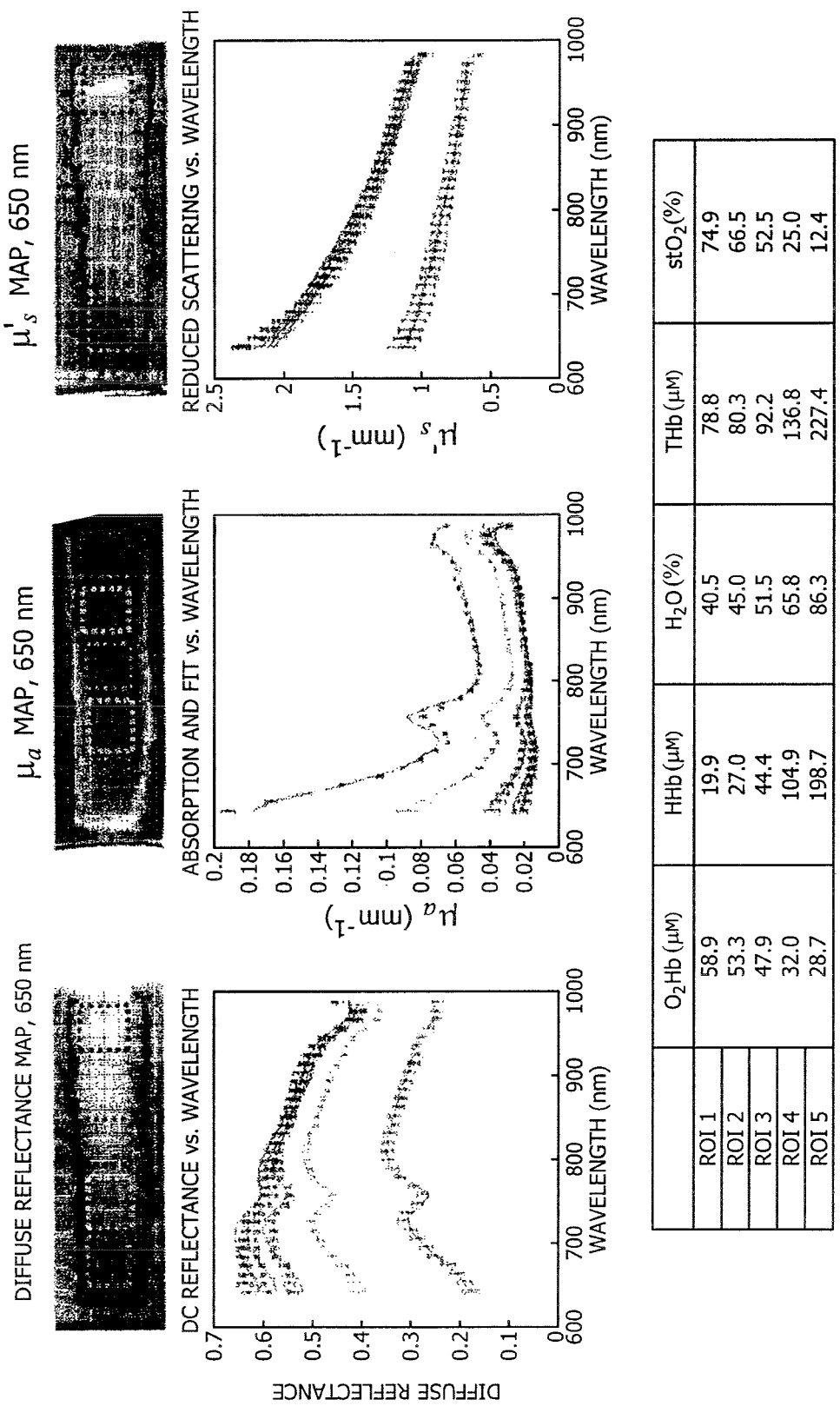
FIG. 3 is a graph of the diffuse reflectance (left), multi-wavelength absorption (center) and reduced scattering (right) properties of a typical in-vivo flap obtained 48 hrs post surgery in a rat model.

A total of 20 rats weighing 300-400 grams were studied. Results depicted in FIG. 3 illustrate multiwavelength absorption and reduced scattering properties of a typical in-vivo flap obtained 48 hrs post surgery. FIG. 3 shows quantitative SI data of the skin flap model 48 hrs post surgery. Measurements were made over a spectral range of 650 to 970 nm using a broadband quartz-tungsten-halogen light source, combined with a liquid crystal tunable filter. Four spatial frequencies were acquired, from 0 mm$^{-1}$ to 0.32 mm$^{-1}$. Moving from the proximal to the distal zone of the flap, we observed 1) a steady increase in total hemoglobin (18-207 µM) and water fraction (28-85%), 2) a reduction in the oxygen saturation (78-25%), and 3) lowered reduced scattering in the distal (necrotic) region. These data demonstrate our ability to map hemodynamic parameters using SI. With the addition of blood flow imaging capabilities of LSI, the metabolic state of each region of tissue can be assessed, giving a more robust indicator of local tissue health. Further small animal studies will develop and validate two-layer models for depth discrimination, develop and validate combined LSI/SI instrumentation for depth-resolved flow, and assess the sensitivity of our depth sensitive chromophore extraction in vivo before moving to clinical studies for peripheral vascular disease, diabetic ulcers and pressure ulcers.

Figure 4A:
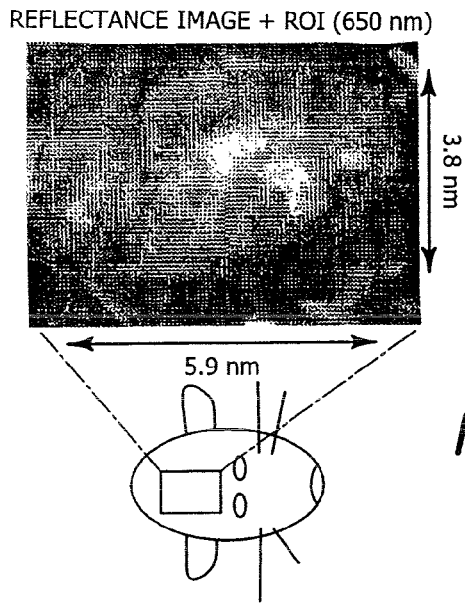
FIG. 4a is a digital map of the planar reflectance and 3.8×5.9 ROI window of cortex at 650 nm.
Figure 4B:
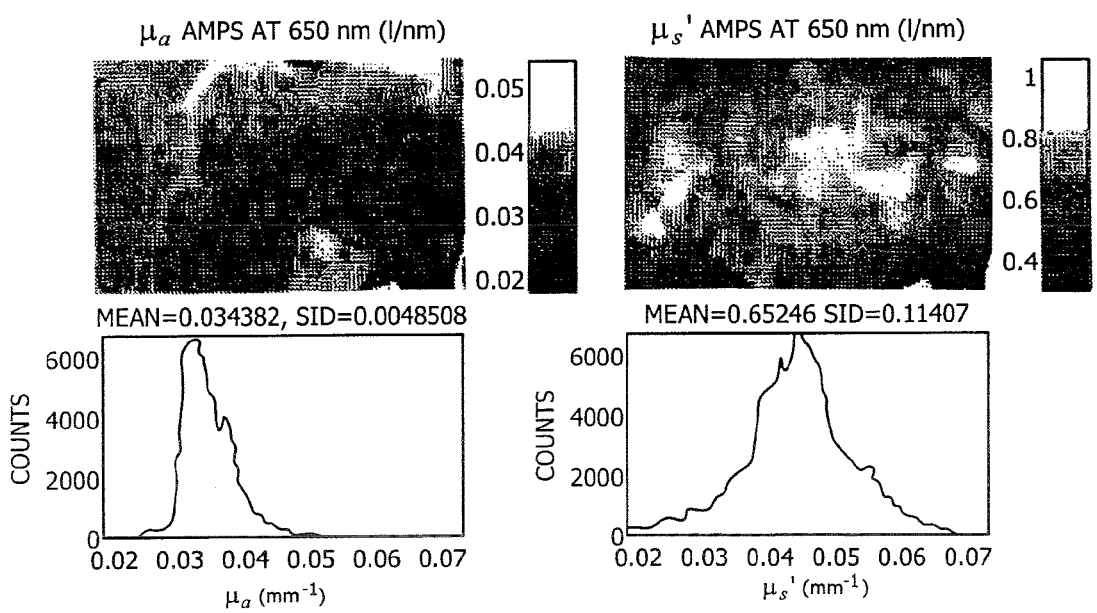
FIG. 4b is quantitative absorption (left) and reduced scattering (right) maps and image histograms. Spatial modulation data were acquired at two spatial frequencies of 0 and 0.13 mm$^{-1}$ over a 5×7 (V×H) mm field of view. For baseline measurements, data were acquired at 10 nm intervals over the entire range between 650 and 980 nm, using a 10 nm bandwidth liquid-crystal tunable filter camera.

Turn now and consider in vivo functional neuroimaging. Proof-of-principle functional measurements have been performed on an in vivo rodent cranial window model. With a dental drill, the skull of the anesthetized rat was reduced to ~100 µm thickness to allow direct imaging of the cortex in this case, the postremedial barrel subfield of the somatosensory cortex. FIG. 4a is a grayscale planar reflectance image of the cortical region at 650 nm. FIG. 4b is an example set of $\mu_a$ and $\mu_s'$ optical property maps and corresponding histograms recovered at 650 nm. A spatially-distinct absorption in the vein region, due to a strong absorption by HHb at this wavelength, was observed, despite the short interaction lengths. We note that the true x-y resolution of optical property contrast spans many detector pixels, as it is fundamentally limited by the physical light transport length scales in tissue, particularly I*=(1/$\mu_{tr}$). Moreover, the contrast from absorbers and scatterers on small spatial scales can display significant partial volume effects (i.e. spatial dilution of optical contrast due to the point spread function of the turbid tissue) in all three spatial dimensions. As part of this embodiment, we quantify these partial volume effects and evaluate models that provide absolute, quantitative and depth-resolved imaging in discrete layers, and tomographic imaging.

Chromophore distribution maps (not shown) were calculated using absorption maps from 650 to 970 nm. In a study of three animals, the average O$_2$Hb, HHb, H$_2$O, THb and stO$_2$ values of three animals were determined to be 57.8±1.7 µM, 39.5±6.3 µM, 66.4±2.2%, 97.4±7.0 µM, and 59.6±3.6%, respectively. Baseline scattering variation between animals was less than 10% at all interrogated wavelengths. The consistency of these results suggests that MI would be useful in longitudinal studies of neurological disease progression and response to therapy.

Figure 5A:
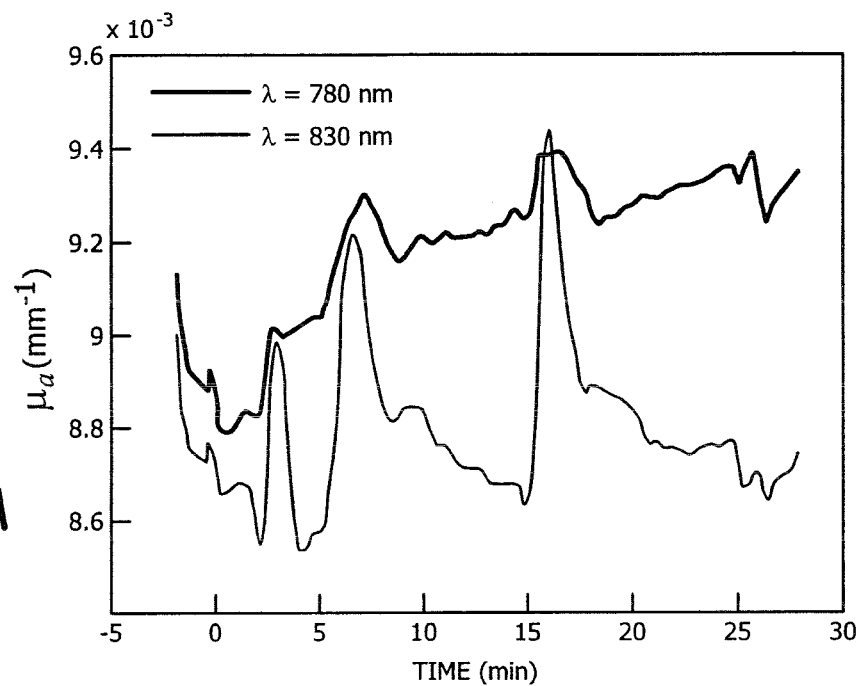
FIGS. 5a-5d are directed to a cortical spreading depression experiment, induced by 1M KCl administration to the cortical surface.
Figure 5B:
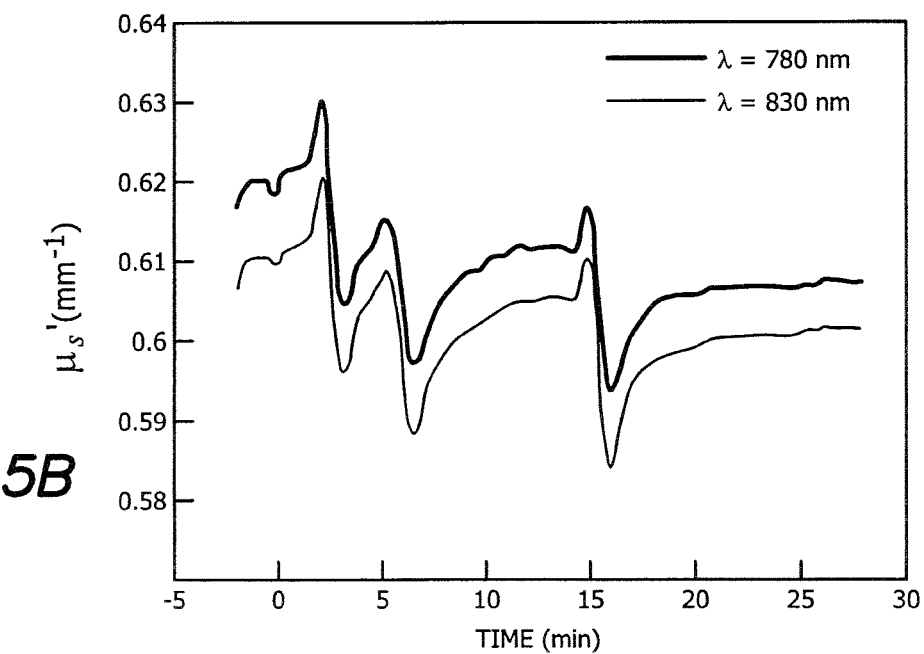
Figure 5C:
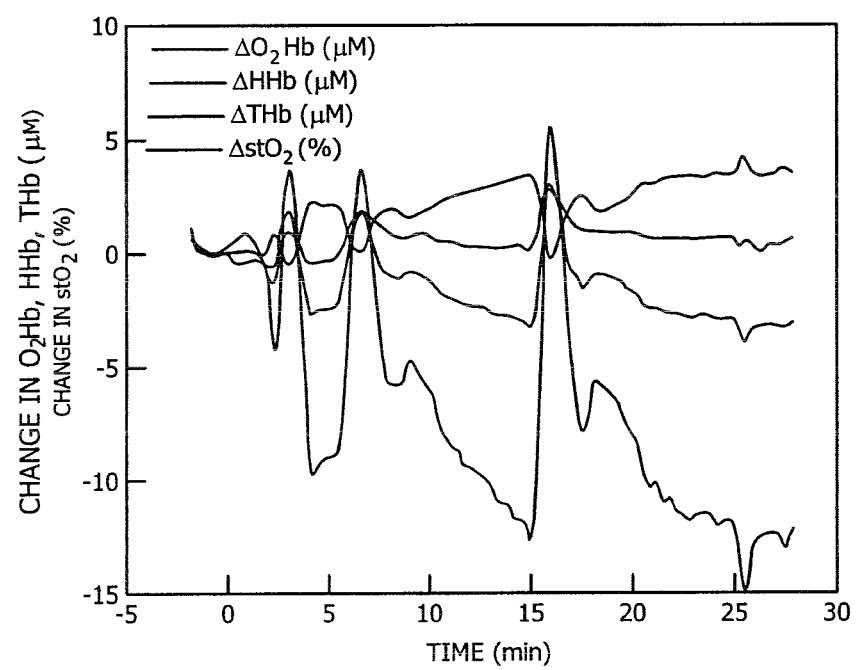
Figure 5D:
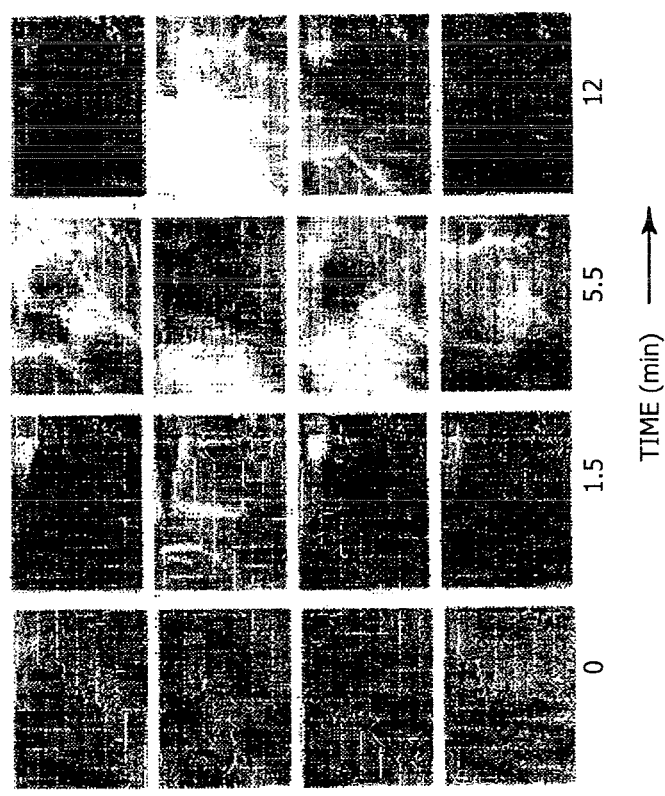
Figure 5E:
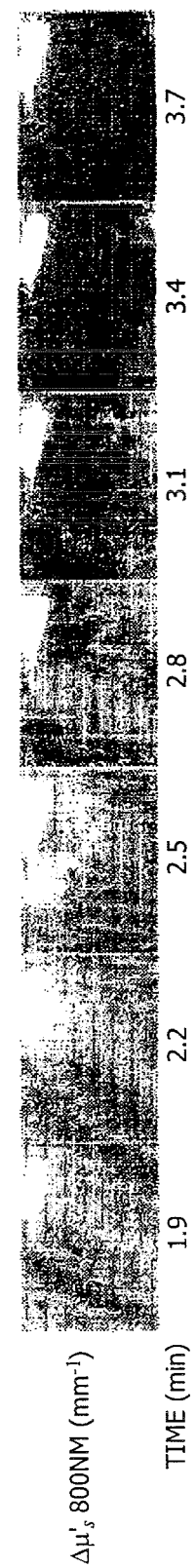
FIG. 5e is a map of reduced scattering coefficient dynamics ($\Delta\mu_s'$) at 800 nm, exhibiting biphasic wave propagating at 2.1 mm/min.

In order to demonstrate the ability of MI to capture and quantify hemodynamic activity in the brain, we induced cortical spreading depression by administration of 1M KCl to the cortical surface at a location above the field of view. MI measurements at 780 and 830 nm wavelengths (two spatial frequencies at each wavelength) were repeated every six seconds for a period of 35 minutes. In FIG. 5a and FIG. 5b, we show graphs of the spatially averaged recovered absorption and reduced scattering coefficients, respectively, measured at 780 and 830 nm. FIG. 5c shows the result of least-squares fitting of the average absorption to $O_2Hb$ and HHb (assuming water content of 80%), as well as calculated THb and $stO_2$ parameters. Note the three large spikes in THb and $stO_2$ due to vascular activity from depression-wave propagation through the measurement field. For each depression wave, we observe an acute increase in 8t02 and blood volume, followed by a slow, sustained trend toward hypoxia and blood pooling in the vein regions. In FIG. 5d, we present chromophore maps at baseline (0 min), hypoxia (1.5 min), hyperoxia+increased blood volume (5.5 min) and long-term blood pooling/deoxygneation (12 min) components of the evoked hemodynamic response. While the absorption changes were associated spatially with vascular hemodynamic changes, the scattering maps in FIG. 5e reveal a slow (2.1 mm/min) propagating biphasic wave, presumably associated with neuronal depolarization. Interestingly, the scattering depolarization wave is clearly followed in space and time by an increase in HHb, $stO_2$, and drop in $O_2Hb$; changes that are consistent with depolarization-induced neural tissue oxygen consumption. This signal presents a novel imaging approach for acquiring electrophysiological information, thus providing a non-contact alternative to microelectrode arrays.

Consider now quantitative broadband snapshot spectroscopy. Integration of a fast 2D hyperspectral imaging technique known as computed tomographic imaging spectroscopy (CTIS) enables fast multi-spectral acquisition of optical property maps. The CTIS device is a spectrometer that uses a 2D holographic grating to simultaneously capture a data cube of spatial and spectral information (x,y,λ) in a single snapshot. We have demonstrated the combination of CTIS with SI using both dynamic turbid phantoms and animal models of epileptic seizure and precursors.

Turn to an application involving dynamic turbid phantoms, where the sample data of a dye mixing experiment (FIG. 6), demonstrates acquisition of hyperspectral images on timescales <1 s that are subsequently rendered into optical property maps. Fast spectral image acquisition is critical to enable rapid data collection in the clinic in order to address time sensitive issues such as patient anesthesia, motion artifacts, and dynamic biological processes. CTIS is implemented in WiFI Instrument #3, to establish the clinical feasibility of WiFI for applications including flap monitoring, port wine stain and melanoma imaging.

Figure 6A:
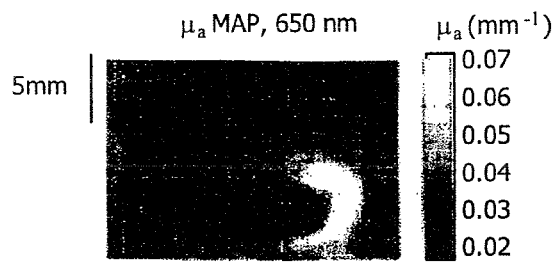
FIG. 6a is a reconstructed absorption coefficient map shortly after injection of one mL of stock nigrosin, with a $\mu_a$ of about 1 mm$^{-1}$ at 650 nm.
Figure 6B:
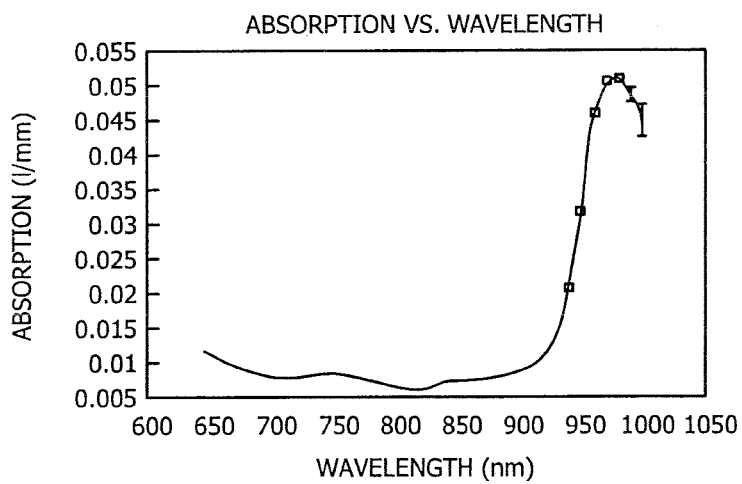
FIG. 6b is a graph of average absorption.
Figure 6C:
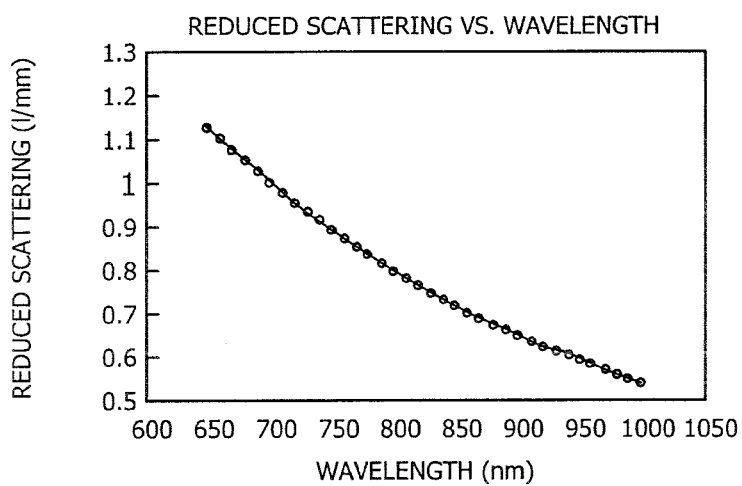
FIG. 6c is a graph of reduced scattering spectra of background (pre-injection) solution of nigrosin, Intralipid and water with properties of $\mu_a$=0.01 mm$^{-1}$ and $\mu_s'$=1.1 mm$^{-1}$ at 650 nm.

FIGS. 6a-6c relate to a mixing experiment demonstrating spectral multiplexing with the CTIS imager. FIG. 6a is a reconstructed absorption coefficient map shortly after injection of one mL of stock nigrosin, with a $\mu_a$ of about 1 $mm^{-1}$ at 650 nm, and average absorption in FIG. 6b and reduced scattering spectra in FIG. 6c of background (pre-injection) solution of nigrosin, Intralipid and water with properties of $\mu_a=0.01$ $mm^{-1}$ and $\mu_s'=1.1$ $mm^{-1}$ at 650 nm. Data acquisition time was about 3 s, demonstrating clinical feasibility of SI for fast, quantitative spectroscopy.

Consider now the use of modulated fluorescence imaging. SI uses spatially-modulated illumination to image tissue constituents. Periodic illumination patterns of various spatial frequencies are projected over a tissue sample. Demodulation of the reflected spatially-modulated waves characterizes the modulation transfer function (MTF) and can be modeled to extract tissue structural and optical property information.

The method has been disclosed in provisional patent application Ser. No. 60/855,526, incorporated by reference, corresponding to a method and apparatus for performing qualitative and quantitative analysis of produce (fruit, vegetables) using spatially structured illumination. However, in that disclosure the method was used within the very limited context of quantitative fluorescence as a means for deducing ripeness of fruit.

FIG. 1b photographically displays the typical data processing flow chart for spatially modulated illumination in the case of an in vivo measurements of a human forearm shown in FIG. 1b, leftmost column, $f_{x,1}$. Intensity data at each frequency $f_{x,2}$, $f_{x,3}$ and $f_{x,4}$ (3 phase images per frequency) are demodulated in the top row of FIG. 1b, calibrated in the second row of FIG. 1b, and fit to yield the spatial maps of the absolute absorption coefficient $\mu_a$ and reduced scattering coefficient $\mu_s'$. Data are processed separately for each pixel, generating spatial maps of optical properties as seen in the bottom row of FIG. 1b. Note the differential contrast in diffuse reflectance ($R_d$) versus spatial frequency ($f_x$) is the basis for quantitative separation absorption and scattering. The processing of the data in SI uses conventional algorithms. See D. J. Cuccia, F. Bevilacqua, A. J. Durkin and B. J. Tromberg, "Modulated Imaging: Quantitative Analysis and Tomography of Turbid Media in the Spatial-frequency Domain," Opt Lett 30 (11), 1354-1356 (2005).

Four evenly spaced frequencies between 0 and 0.15 $mm^{-1}$ were collected at a wavelength of 640 nm. The differential contrast observed as illumination frequency increases is the basis for the quantitative separation of absorption and scattering. As shown in the final absorption map of FIG. 1b, vein structure can be clearly visualized due to absorption contrast. Also, a vertical feature of lower scattering is evident in the middle of the scattering map on the bottom right image of FIG. 1b, which is coincident with a large superficial tendon.

When combined with multi-spectral imaging, the extracted optical properties at several wavelengths can be used to determine the in vivo local concentrations of chromophores such as oxy- and deoxy-hemoglobin, water and lipid. Furthermore, images at various spatial frequencies can be processed to visualize depth-sectioned subsurface features in terms of scattering and absorption. SI shows potential as a quantitative fluorescence imaging system that can extract both quantum yield and concentrations of fluorophores in turbid media with depth sensitivity.

A standard reflectance SI system demonstrates the ability to calculate optical properties at a single wavelength. We can create a fluorescence SI imaging system by placing appropriate dichroic bandpass filters at the excitation wavelength and emission wavelength for the source and detector respectively.

FIG. 1a illustrates the platform generally denoted by reference 10 used for spatial modulation of NIR light. A simple digital projector 12 (NEC HT1000), based on a digital micromirror DLP light engine (Texas Instruments), and a UHP mercury lamp 16 are used to generate the structured or spatially modulated light. The projector's color filter wheel 18 was removed, producing a broadband "white light" illumination of the sample. Interference filters can be placed for narrow detection of a specified wavelength. The diffusely reflected light is captured by a 16-bit frame-transfer CCD camera 22 (Roper Cascade 512F at 512×512 resolution). Cross-linearized polarizers 20 are also introduced at the source 16 and detector 22 to eliminate specular reflectance. Camera 22 is coupled to computer and display 24 which controls platform 10 to provide scanned maps and to process the data according to the disclosed methodology to produce the maps of the figures using conventional software and the disclosed conventional algorithms.

In the illustrated embodiment, the fluorophores Cy5.5 and Alexafluor 680 (Invitrogen) were the chosen the inclusions in our phantoms only as an example. Both these fluorophores have a peak excitation at 680 nm. In order to obtain fluorescence data and maintain spectral separation between excitation and emissions, the sample 14 was excited with the placement of an interference filter 20 ($\lambda$=660 nm, $\delta$=10 nm FWHM) at the source 16 (UHP mercury lamp) and the emission was detected with a filter 20 ($\lambda$=720 nm, $\delta$=10 nm FWHM) placed in front of a CCD camera 22 (Roper Cascade 512F). Standard Reflectance data were collected at 660 nm and 720 nm by placing the appropriate band-pass filter (not shown) at the detector and source respectively.

All samples 14 were illuminated at 12 evenly spaced spatial frequencies between 0 and 0.45 mm$^{-1}$. The subsequent data were there demodulated as demonstrated by Cuccia in the above citation by conventional methods. Optical properties were calculated in reflectance mode at the excitation and emission wavelengths by using a lookup table of diffused reflectance values plotted against optical properties and spatial frequencies. This lookup table was generated using forward Monte Carlo simulations. Two frequencies, 0 and 0.2 mm$^{-1}$, were used to extract the optical properties as they provided adequate absorption and scattering contrast. A calibration phantom with known optical properties was measured at each wavelength in order to correct for the system response.

The illustrated embodiment was carried out on tissue-like gelatin phantom samples 14 conventionally fabricated as described in A. M. De Grand, S. J. Lomnes, D. S. Lee, M. Pietrzykowski, S. Ohnishi, T. G. Morgan, A. Gogbashian, R. G. Laurence and J. V. Frangioni, "Tissue-like phantoms for near-infrared fluorescence imaging system assessment and the training of surgeons," J Biomed Opt 11 (1), 014007 (2006). Briefly, a 7.5% gelatin mixture was created in TBS solution in order to maintain a tissue-like pH of 7.4. The absorption and the scattering were controlled by introduction hemoglobin and Intralipid respectively. For demonstration of qualitative fluorescence imaging, a two layer gelatin phantom was fabricated with a 1 mm top layer ($\mu_a$=0.01, $\mu_s'$=1) and semi-infinite bottom layer with a fluorescent background (0.1 µM Cy5.5 equivalence). Three one-mm-diameter beads tagged with 1 µM Cy5.5 equivalence were placed just below the surface and at depths of 1 mm and 2 mm. The deepest bead was in the fluorescent background part of the phantom while the middle bead and the shallowest bead were not in a fluorescent background.

Figure 7A:
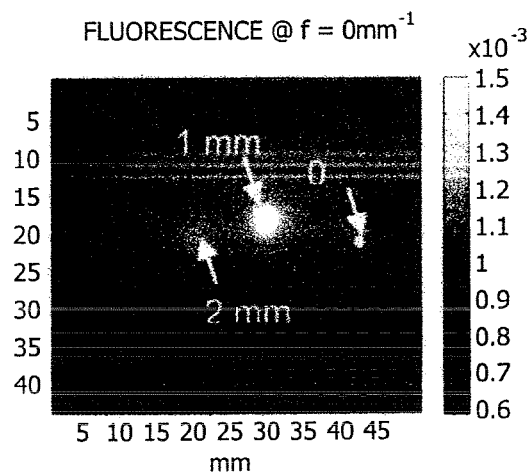
FIGS. 7a-7e are the first demonstration of modulated fluorescence imaging for depth discrimination of fluorophores.
Figure 7B:
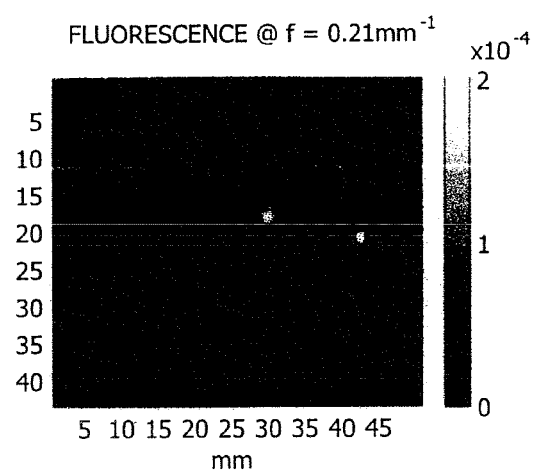
Figure 7C:
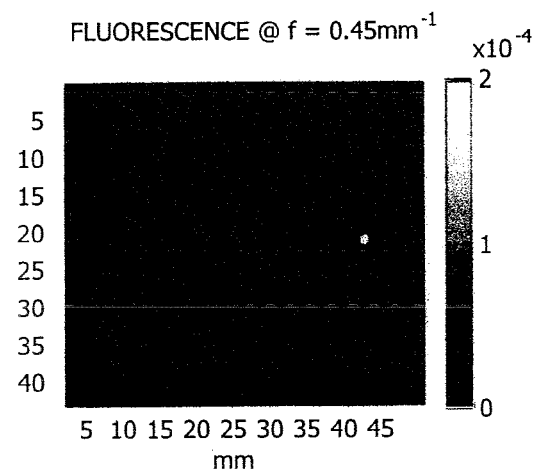
Figure 7D:
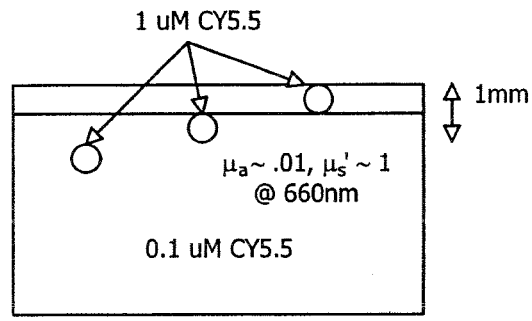
Figure 7E:
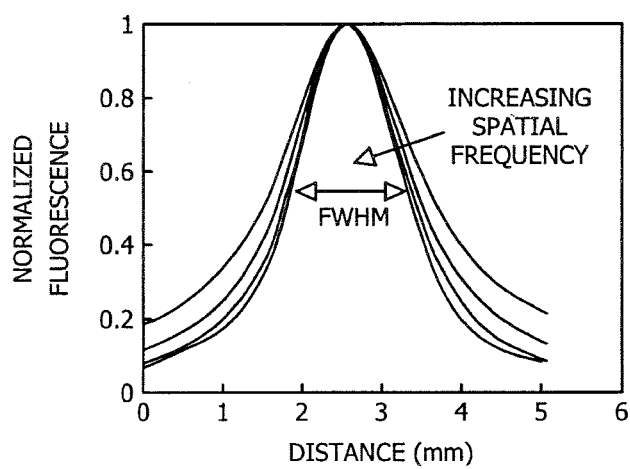

In FIGS. 7a-7c, the fluorescence image demonstrates the visualization of the three beads at all depth locations. Each bead appears to have a different diameter due to the diffuse effects of the fluorescence coming back to the surface. The introduction of a higher spatial frequency illumination (f=0.21 mm$^{-1}$, FIG. 7b), suppresses background fluorescence as well as the deeper 2 mm bead. Finally, the introduction of an even higher spatial frequency in FIG. 7c reduces further the background fluorescence and permits visualization only of the surface bead dramatically, thus improving the signal-to-noise ratio. Additionally, the apparent bead size decreases as the spatial frequency of the excitation light increases as shown in the graph of FIG. 7e. This is demonstrated by taking a linear profile of the most superficial bead and comparing the full width at half maximum for 5 different spatial frequencies. The depth sectioning phenomena and improvement in resolution are presumably due to the smaller interrogation depths expected at higher spatial frequencies.

This is the first system that can provide a wide-field quantitative fluorophore quantum yield (QY) map in turbid media. In the past, a molecule's quantum yield was calculated in solution as an average value over a large homogeneous volume using spectroscopic techniques. Thus, there was no way to map quantum yield over a specific region of interest or to differentiate between types of fluorophores. Due to the wide-field imaging capabilities of the structured illumination methodology, there is now a way to resolve quantum yield between two separate fluorophore concentrations and potentially different fluorophores in the same solution.

Figure 8A:
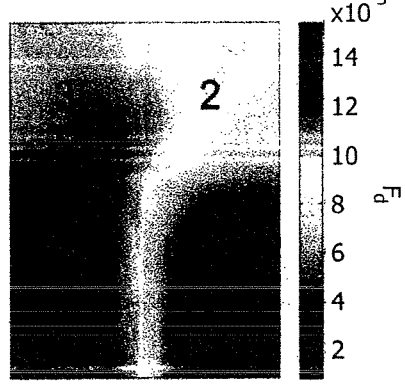
FIGS. 8a-8d demonstrate a quantum yield computation. The phantom illustrated in these photograph measured by SI consists of 4 quadrants of increasing fluorophore concentrations.
Figure 8B:
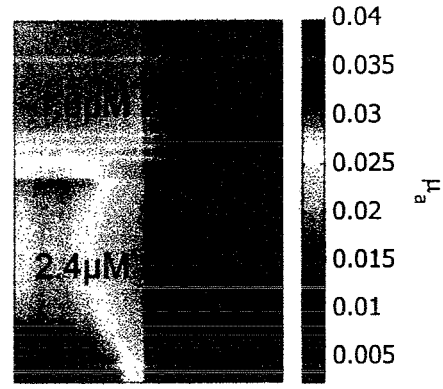

The fluorescence quantum yield (QY) is the ratio of number of emitted fluorescence photons to the number of absorbed photons. Quantum yield is an intrinsic property of the fluorophore and is independent of molecular concentration. Quantum yield can be affected by tissue environmental factors, such as pH, and thus can serve as a sensitive indicator of functional tissue status (i.e., hypoxic conditions). To evaluate the ability of modulated fluorescence imaging to study quantum yield, we created a tissue phantom 14 containing four homogenous quadrants of Alexafluor 680 with varying concentrations (0, 0.8, 1.6, and 2.4 µM). Reflectance images at the excitation and emission wavelengths were acquired as well as a fluorescence image. The demodulated fluorescence and absorption maps are shown FIGS. 8a and 8b. If we average all the pixels in the respective quadrants, our extracted fluorescence reflectance map (FIG. 8a) and absorption map (FIG. 8b) show a linear relationship between the absorption coefficient and fluorophore concentration as graphed out in FIG. 8d. A previously derived conventional intrinsic fluorescence transport model is used to extract QY. See J. Wu, M. S. Feld and R. P. Rava, "Analytical model for extracting intrinsic fluorescence in a turbid medium," Appl Optics 32 (3585 (1993). Briefly, Wu et al. describe a diffusion based model for modeling fluorescent light transport in homogenous media. In this model, the excitation source is modeled as it arrives at the fluorophore and the emitted fluorescence treated as a separate source that propagates to the surface. This diffusion based transport model depends on background optical properties of the sample in order to extract the quantum yield. Thus, background optical properties are needed for both the excitation and emission wavelength, which can be calculated using a Structured illumination reflectance mode at these two wavelengths. The relationship between the excited and emitted light is correlated in the model by some unknown constant or the quantum yield.

Figure 8C:
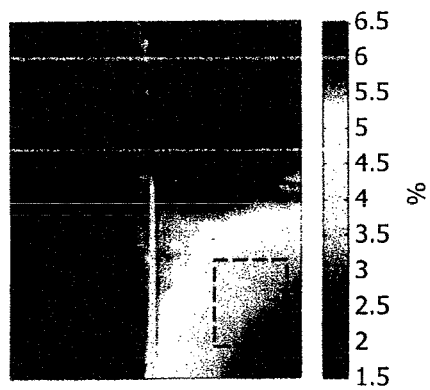
Figure 8D:
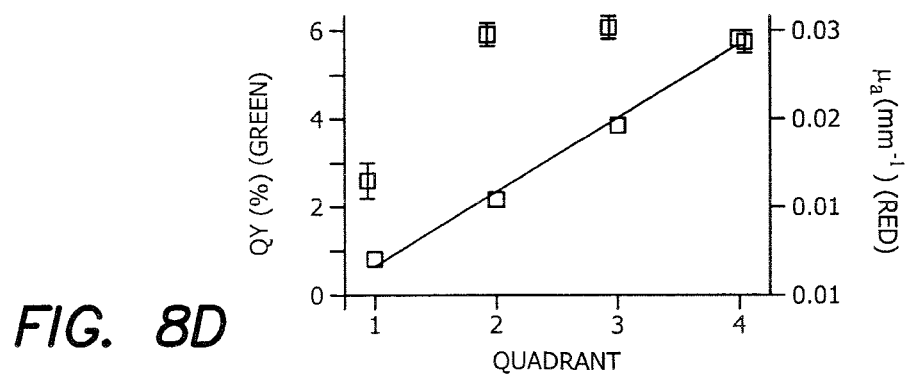

The combination of a fluorescence map and optical property maps at the excitation and emission wavelengths can be used to compute a quantum yield map as shown in FIG. 8c. In order to calculate quantum yield, the measured fluorescence by SI is divided by the theoretical fluorescence as described by the model and the optical properties extracted in reflectance mode. Measured fluorescence is also reduced due to the spectral inefficiency of the interference filters used at the detector. This loss in measured fluorescence is corrected for when displaying fluorescence maps. The theoretical fluorescence is calculated by assuming 100% quantum yield. Thus, the ratio of the two maps, measured fluorescence and theoretical fluorescence, represents the quantum yield of the fluorophore. Once again, if we average the pixels within each quadrant, we see that the quantum yield is the same for all the fluorophore filled quadrants 2-4 and different for the quadrant 1 without fluorophore as best shown in FIG. 8d.

The illustrated embodiment demonstrates both qualitative and quantitative abilities to perform fluorescence imaging using Structured illumination. Qualitatively, we have demonstrated both depth sensitivity and resolution improvements as a function of depth sensitivity. The depth sensitivity shows that SI has the potential as a near real-time depth sectioning tool for in vivo fluorescence imaging.

Additionally, the combination of tumor specific exogenous contrast agents and improved resolution due to SI has potential in tumor margin delineation during surgery.

Lastly, we show that depth sensitivity varies as a function of spatial frequency. This suggests that SI has the potential as a quantitative tomographic imaging modality.

In addition, we have also demonstrated the ability of SI to generate quantum yield maps. This demonstrates that we have the potential to identify specific exogenous fluorophores independent of concentration. These preliminary data show SI has potential as a tool to track fluorophores in vivo, separate exogenous fluorophores from autofluorescence, and determine whether the fluorophore is in a bound or unbound state.

This disclosure thus represents an enabling description of the method and first results obtained within the context of molecular imaging, for example for clinical and pre-clinical applications.

This is the first quantitative wide-field mapping of quantum yield in turbid media to our knowledge. This will allow the user to image multiple fluorophores in the same image and not have to average them together for a single bulk measurement. Additionally, the quantum yield of fluorophores in different states (pH difference or bound) can be resolved and identified.

This methodology will provide a way to map and characterize fluorophores in wide-field fluorescence imaging applications. For example, this technique could be incorporated into an intra-operative system to help identify exogenous fluorophores and differentiate from auto-tissue fluorescence as well as bound and unbound states of a fluorophore. This could potentially allow the surgeon to clearly identify tumor margins during tumor resection.

In addition, this approach enables imaging the quantum efficiency in 2- or 3D within a turbid medium. This enables location and quantization of fluorescence-related phenomena on a concentration-independent basis. This data can provide new metrics of local tissue status. For example, when coupled with a fluorophore whose quantum yield has a dependence on pH, local tissue pH can be probed and measured in a non-invasive, non-contact fashion. This information could be used, for example, to assess the local chemical and metabolic state of a tumor in-vivo, which could have a particularly strong impact in the application areas of small animal imaging, high-throughput screening of thick tissue specimens, and medical diagnostics.

Figure 9:
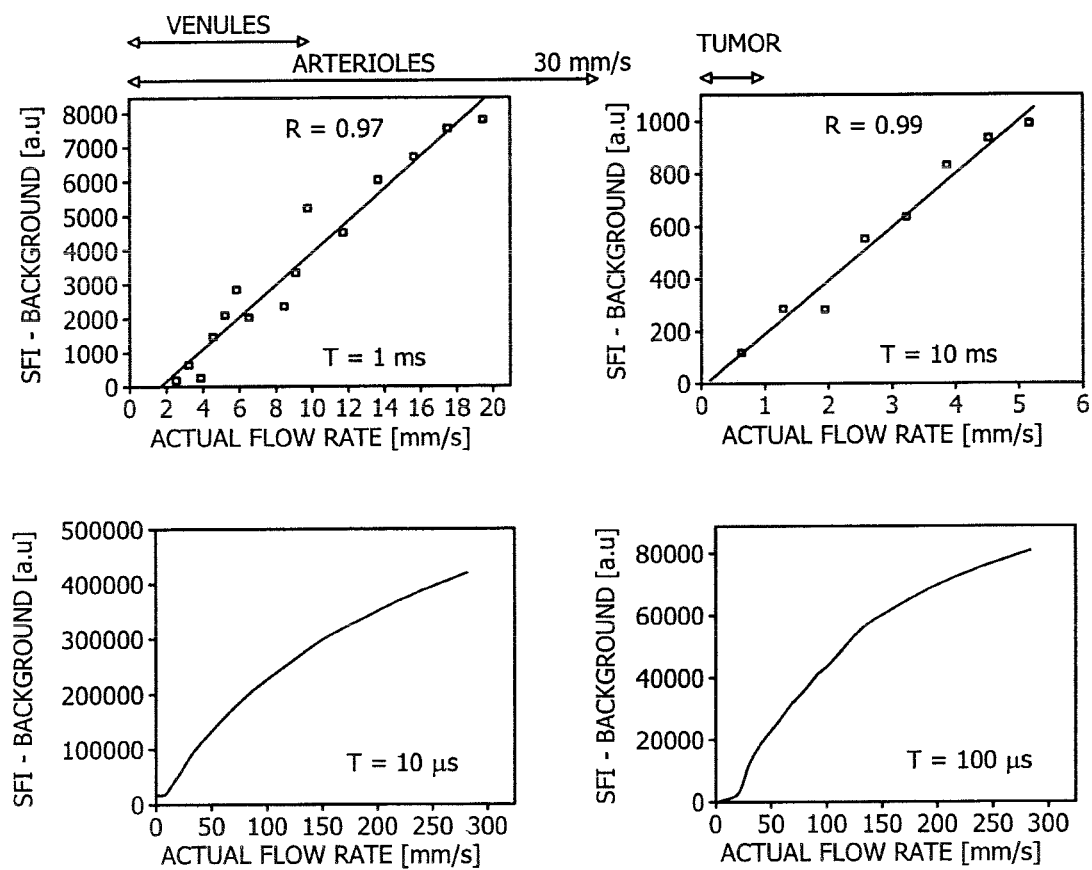
FIG. 9 is four graphs of background-corrected speckle flow index values are affected by speckle image exposure time. The data show that the blood vessel types (tumor flow, arterioles/venules, arteries/veins) that can be assessed in a linear fashion depends critically on image exposure time.

Consider now laser speckle imaging LSI in wide field blood flow rate characterization. With judicious selection of speckle image exposure time, blood flow rate characterization spanning tumor vasculature to arteries in small animal models is achievable. To estimate the linear response range of LSI, we performed experiments on tissue-simulating flow phantoms. With an infusion pump, whole human blood was flowed through tubing embedded near the surface of either agar gel or silicone. As can be seen from the data in FIG. 9, we conclude that image exposure time affects linear response range. With use of common exposure times (1-10 ms), our data suggest it is possible to characterize blood flow in sluggish-flow conditions (i.e., tumor vasculature) and in arterioles and venules. With a further decrease in exposure time, the linear response range shifts towards flow rates that are typical of small-animal arterial blood flow. For example, the common iliac artery (0.5 to 1.0 mm in diameter) in mice has an approximate flow rate of 150 mm/s. These preliminary data are important, because they demonstrate that with appropriate selection of exposure time, a linear relationship exists between speckle flow index and actual blood flow rate. This outcome is important for accurate calculation of metabolic dynamics (i.e., $CMRO_2$).

Figure 10:
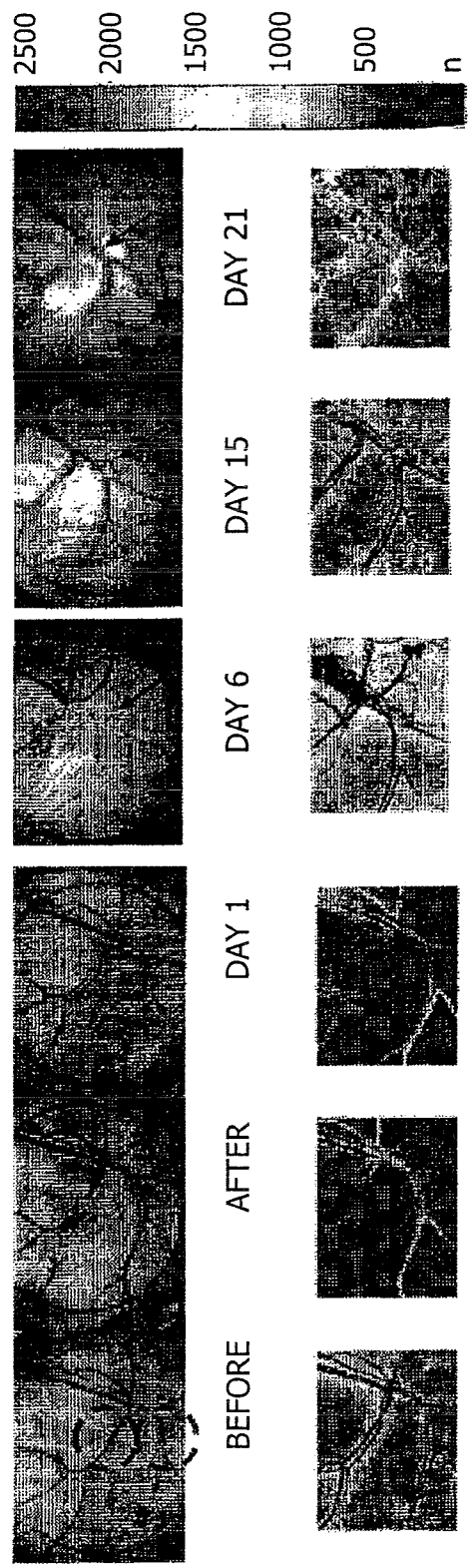
FIG. 10 is a series of micrographs of vascular remodeling and blood flow dynamics were evident during the 21-day monitoring period, with the Day 0 and Day 21 structural images having similar appearances.

FIG. 10 is a series of micrographs of vascular remodeling and blood flow dynamics were evident during the 21-day monitoring period, with the Day 0 and Day 21 structural images having similar appearances. A time sequence of wide-field color reflectance images (top row) and corresponding speckle flow index images (bottom row) was acquired over a 21-day monitoring period after pulsed laser irradiation of selected sites. Two arteriole-venule pairs (dashed circles in "Before" image) were irradiated with simultaneous 532 and 1064 nm laser pulses (upper circle—five 1-ms laser pulses at 27 Hz repetition rate, 2 J/cm$^2$ at 532 nm, 3.6 J/cm$^2$ at 1064 nm; lower circle—single 1-ms laser pulse, 4 J/cm$^2$ at 532 nm, 7.2 J/cm$^2$ at 1064 nm). The color reflectance image dimensions (H×V) were: 13×10 mm$^2$. SFI image dimensions were: 9×7 mm2

Turn to LSI flowfield characterization of microvascular response to laser therapy. The short-term (<<24 h) microvascular response to light-based therapeutic intervention differs considerably from the long-term response. To study the microvascular response to a novel laser-based treatment protocol, we applied LSI in experiments involving the rodent dorsal window chamber model. Previous studies have been restricted to short-term evaluation, due primarily to problems with animal model preparation. As can be seen from the data in FIG. 10, we conclude that the short-term and long-term microvascular response to treatment differ considerably. The short-term response was characterized primarily by photocoagulation events, with a substantial-to-complete venular flow reduction and considerable arteriolar flow reduction. At 24 h post-intervention, the arteriolar flow (circle in Day 1 speckle flow index image) was absent. At later time points, partial to complete restoration of blood flow in these photocoagulated vessels was observed (FIG. 10). In general, we observed a variety of microvascular dynamics, including vasoconstriction, vasodilation, and delayed blood flow changes, in both directly irradiated and nonirradiated vessels. We have observed shunting of blood flow to tortuous collateral vessels (i.e., indicated by arrow in Day 6 image). Furthermore, we have observed vessel repair within the same position as the original vessel (i.e., indicated by arrows in Day 15 and Day 21 images), suggesting that the vascular remodeling process may be associated with a "memory", in agreement with published tumor angiogenesis data. Collectively, these data provide a key part of the motivation for this proposal. With LSI alone, we identified flow redistribution and remodeling of the microvascular architecture through established animal models, but we did not have access to the underlying mechanisms inducing the observed response. The ability to quantitatively assess molecular reporters related to angiogenesis (i.e., vascular endothelial growth factor) has the potential to enable studies of biochemical processes underlying the microvascular response to light induced injury with the goal of applying ensuing therapies that target these processes.

In conclusion, we have presented SI and LSI studies in vitro and in vivo that validates their feasibility and richness in functional information content as stand-alone modalities. We have combined these modalities in order to develop a single integrated WiFI platform capable of absolute depth resolved quantification of tissue absorption, scattering, fluorescence, and blood flow. The resulting technology will provide researchers with the quantitative tools necessary to study disease progression and therapeutic response in vivo.

Consider SI and LSI integration. Successful integration of reflectance/fluorescence SI and LSI methodology into single-platform WiFI instruments requires: 1) that two-dimensional (Instrument 1) maps of absorption, scattering, and blood flow result from optical interrogation of known tissue volumes, 2) that three-dimensional (Instruments 2 and 3) maps of absorption, scattering, fluorescence, and blood flow are coregistered, and 3) that fundamental constraints imposed by each imaging modality are satisfied within each single-platform embodiment.

This includes consideration of the origin of speckle contrast perturbations in relation to absorption characteristics extracted with SI methods. Regarding condition 3, the following parametric constraints must be considered to satisfy the individual requirements of reflectance SI and LSI:

a. For SI, lens magnification, camera pixel pitch, and spatial frequency of structured illumination collectively must satisfy the Nyquist sampling criterion.

b. For LSI, lens magnification, camera pixel pitch, and lens f-stop should satisfy the following equation: $d=1.2(1+M)\lambda(f/\#)$ where d is the pixel pitch, M is the lens magnification, $\lambda$ is the light source wavelength, and f/# is the lens f-stop.

c. For LSI, light with a long coherence length (i.e., greater than the mean path length of multiply scattered remitted light) must be used in order to generate a high-contrast speckle pattern.

d. The light source must have sufficient power to fill the camera dynamic range (for reflectance SI) and to generate sufficient reflected intensity given the short (~10 ms) exposure time and lens aperture constraints defined in 2).

Constraints 1 and 2 require selection of appropriate cameras and lenses to satisfy the demands of both SI and LSI. As a specific example, the Dalsa Pantera camera to be used with WiFI Instrument 1 has a 1024×1024 pixel array with a pixel pitch of 12 μm. To achieve a 1 cm×1 cm field of view, a lens magnification of 0.8× is required. For LSI, the appropriate f-stop setting would be 8, which is readily achievable with standard macro lenses. As the magnification decreases (i.e., expanding the field of view to a 10 cm×10 cm field of view, as in Instruments 2 and 3), the upper limit (M→0) on the f-stop is 12, which also is readily achievable with standard macro lenses. To address constraints 3 and 4, we will use high-power (about 50 mW) 785 and 820 nm diode lasers with long (centimeters) coherence lengths.

Consider the development and validation of models of light propagation and characterize WiFI contrast/resolution using heterogeneous tissue-like phantoms and appropriate numerical simulations. Model development and validation studies result in the development algorithms for multi-layer geometries, fluorescence tomography, and the combined SI/LSI platform. In parallel, we assess basic spatial resolution capabilities of our WiFI instruments.

Consider quantitative optical imaging and modeling in turbid media. In general, fundamental light propagation models are generated and algorithms validated experimentally through measurements of tissue-like phantoms (Table 1). First, analytical and statistical multi-layer models (standard diffusion approximation (SDA), Monte Carlo (MC), and $\delta$-$P_1$) are developed and validated with measurements of multi-layer gelatin phantoms containing varying layer thickness and optical contrast. The measurements use new multi-layer algorithms to extract optical properties in order to validate our models and determine our system's ability to resolve both lateral and axial optical contrast in layered systems. Second, fluorescence radiative transport (FRT), tomography, and LSI/SI flow models are developed and validated experimentally with inclusion phantoms. These phantoms feature absorption/fluorescence inclusions of variable sizes (200 μm-2 mm diameter), variable physiological concentrations (0-100 μM), variable separations (0-50 mm), and variable depths (0-50 mm). The inclusions are either tubes to simulate vasculature/flow conditions or beads to simulate tumors. The locations of these inclusions will also allow us to determine the ability of our WiFI instrument to resolve sources of contrast at a given separation and/or depth.

TABLE 1

Summary of Phantom Validation Studies

| | Multi-layer phantoms | Perturbation Phantoms |
|---|---|---|
| General Phantom Design | 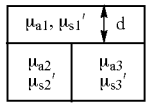 | 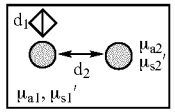 |
| Key Phantome Features | Vary optical properties in each layer<br>Vary layer thickness (d) | Fluorescent/absorption perturbations at depth<br>Tube perturbations with flow<br>Bead perturbations<br>Perturbation separation |
| Primary Models Developed and Validated | Multi-layer SDA<br>Multi-layer MC<br>Multi-layer $\delta$-$P_1$ | Fluorescence Radiative Transport (FRT)<br>Tomography<br>LSI/MI flow validation |
| Collaborations | VP: VTS<br>VP: Small Animal ATK<br>Dr. Stuart Nelson | VP: Small Animal ATK (FRT)<br>Dr. John Frangioni (FRT)<br>Dr. James Tunnell (tomography)<br>Dr. David Boas (LSI/MI) |
| Applications | Quantitative Planar Imaging<br>Brain (skull/brain)<br>Tumor (skin/tumor)<br>Skin (melanin/skin) | Small animal tomography<br>$CMRO_2$ validation |

Along with the in vitro phantom validation studies (Table 1), there are vivo validation studies. We perform both systemic and localized perturbations to the exposed microvascular network of rodent window chambers. We have extensive experience with the dorsal window chamber in mice, hamsters, and rats. With this model, we have unique access to both the epidermal and subdermal sides of skin, with thicknesses ranging between about 300 μm (mouse) to about 2 mm (rat). Thus, we can characterize quantitatively both superficial tissue characteristics (i.e., direct imaging of the subdermal microvascular network) to assess the true tissue metabolic state, and subsurface tissue characteristics (i.e., imaging from the epidermal side) to evaluate WiFI accuracy in a more realistic tissue geometry. To evaluate the ability of WiFI to image large-scale metabolic changes, we use established methods: 1) vasoactive agents (acetylcholine for vasodilation, norepinephrine for vasoconstriction) administered via tail-vein or jugular-vein catheters, and 2) thermal interventions (low-irradiance argon laser heating of the microvasculature, circulating cold water at a set temperature). With the therapeutic laser systems available at BU, we investigate the focal changes in tissue metabolism induced with pulsed laser irradiation. In general, we expect to observe an increase (decrease) in tissue metabolism with a decrease (increase) in blood flow. Furthermore, we expect to observe co-localization of blood flow and regions of high total hemoglobin content, which is a key validation step demonstrating successful fusion of SI and LSI.

We anticipate that the primary bottleneck in practical application of WiFI instrumentation, especially in the clinic, will be MI data acquisition time. LSI acquisition times are insignificant (about 100 ms) compared to SI acquisition times. In SI, we generally acquire up to thirteen spatial frequencies and thirty wavelengths (about 6 minutes acquisition time) for our current MI studies and reduce our dataset during postprocessing steps in order to extract the desired chromophores and to obtain depth selectivity. The current imaging platform is capable of acquiring reflectance maps at two spatial frequencies and three phases at a rate of 1.5 s per wavelength. This is the first work that quantitatively assesses the minimum number of required spatial frequencies and interrogated wavelengths for accurate chromophore extraction and depth selectivity in a clinical situation. This work sets the benchmark in minimizing acquisition schemes.

Processing time is also an obstacle to achieve our goal for real-time visualization. We expect that hardware and software advances focused on parallel processing schemes and tools, such as graphics processor units (GPU), will shorten analysis time to achieve near real-time (about 20 frames per s) imaging rates. All the WiFI instruments include the hardware resources to permit fast data analysis as needed and reduce the bottleneck for visualization to acquisition schemes.

We expect to have an optimized, validated set of WiFI image processing algorithms to perform quantitative depth-resolved characterization of absorption, scattering, fluorescence, and blood flow along with a firm understanding of the resolution and contrast limitations of our WiFI instrumentation.

The WiFI instrument embodiments have 1) real-time (20 frames per second) optical neuroimaging; 2) whole-body, small animal tomographic imaging; and 3) clinic-friendly spectroscopic imaging. The integration of SI, LSI, and fluorescence imaging for instrumentation development based on our research needs has the objective to design and fabricate three multimodal WiFI instruments designed to address three specific application categories: 1) real-time optical neuroimaging; 2) whole-body, small animal tomographic imaging; and 3) clinic-friendly spectroscopic imaging. This is an illustrative set of embodiments and is not intended to limit the scope of the invention.

Figure 11A:
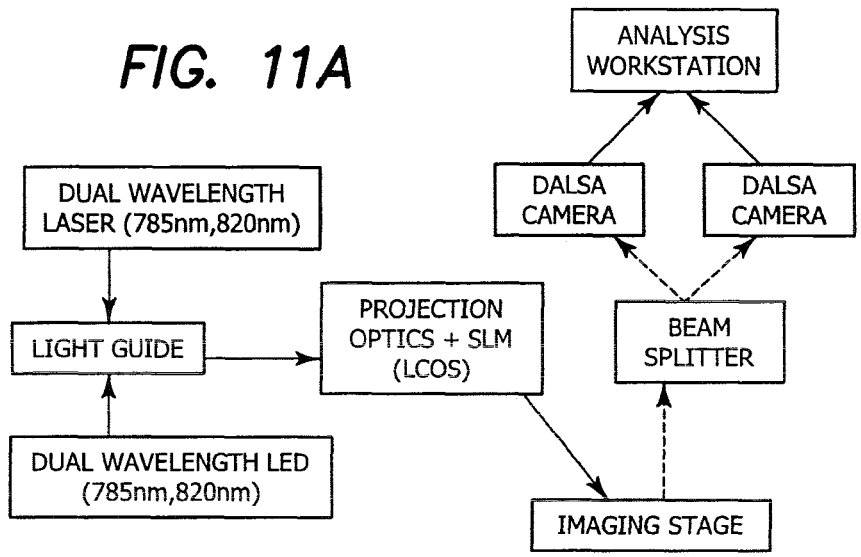
FIG. 11a is a schematic of WiFI instrument 1 which is a small field-of-view (1 cm×1 cm), dual wavelength (LED or laser), dual frequency system.
Figure 11A:
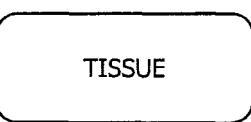
Figure 11B:
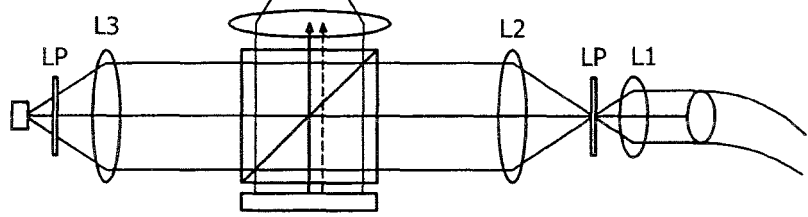
FIG. 11b is a diagram of a LCOS spatial light modulator to permit laser projection with a motion-free system.

We focus our instrument fabrication efforts to address specific preclinical and clinical needs. Consider the real-time optical neuroimaging instrument (WiFI Instrument 1). The multimodal neuroimaging instrument performs fast and quantitative optical metabolic imaging of the brain. This system combines reflectance/fluorescence SI and LSI imaging techniques for the first time. In order to optimize speed, WiFI instrument 1 is a small field-of-view (1 cm×1 cm), dual wavelength (LED or laser), dual frequency system targeted at real-time (20 fps) measurement, analysis, and visualization of dynamic neural signals such as stroke and epilepsy (FIG. 11 a). The system is based on a LCOS spatial light modulator (FIG. 11 b) in order to permit laser projection with a motion-free system (preventing speckle dephasing in the instrument itself). In order to achieve maximal acquisition rates, both projection and detection arms are spectrally multiplexed with a dichroic combiner and splitter, respectively. Dual-CCD detection is provided by Dalsa Pantera 1M60 camera-link devices. Both cameras and the LCOS developer's board is synchronized at 60 frames per second via hardware triggering, projecting 3 phase patterns at a rate of 20 Hz. Acquired data are 1) frequency-demodulated, and 2) calibrated, then 3) processed into absorption and reduced scattering optical property maps using an established rapid lookup table approach, then 4) processed into chromophore maps with linear spectral analysis of the multispectral absorption data. Parallelized code operating on an eight-core workstation performs these four processing components simultaneously with computational power to spare for user-GUI interaction and visualization. The acquisition, control, processing and visualization code for this instrument is based on the MI Inc. C#/C++ acquisition framework. The most demanding challenge is to implement the "measurement loop" for this instrument (i.e. tight synchronization of hardware and analysis components to achieve the proposed 20 fps frame rate) which requires the development of hardware specific drivers as well as analysis code in C#.

Figure 12A:
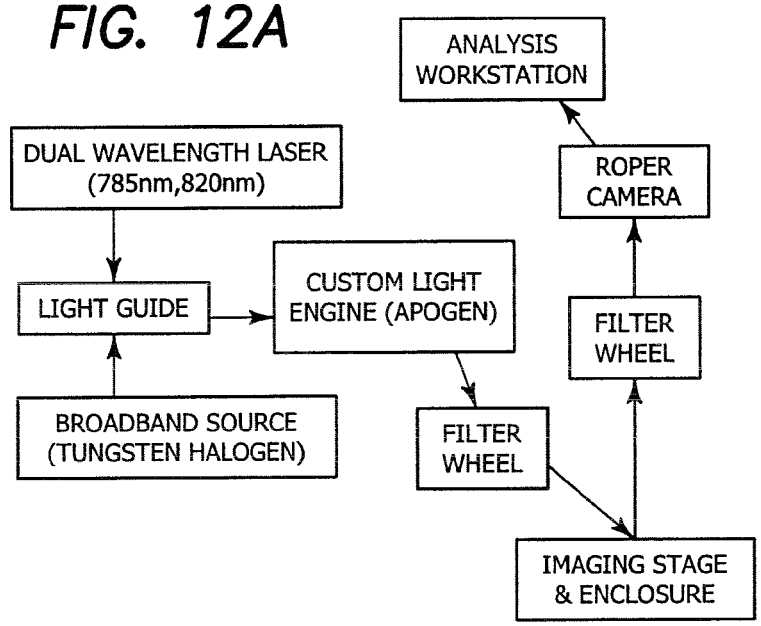
FIG. 12a is a block diagram of a small animal tomographic imaging instrument (WiFI instrument 2) which is fabricated for the primary purpose of tumor angiogenesis studies.
Figure 12B:
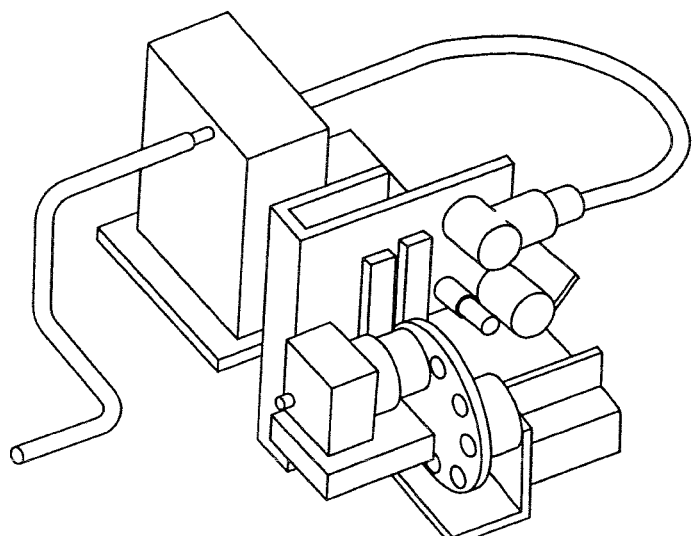

Consider now the small animal tomographic imaging instrument (WiFI Instrument 2). A small animal tomographic imaging instrument (WiFI instrument 2) is fabricated for the primary purpose of tumor angiogenesis studies. A light-tight enclosure allows 3D measurement, analysis, and visualization of endogenous and exogenous fluorescence, absorption and scattering contrast (FIG. 12a). The system is based on a custom-built, digital micromirror device (DMD)-based light engine (DVImage developer's kit, Apogen Inc.) for near-infrared (NIR) structured light illumination (FIG. 12b). For detection, this system incorporates a back illuminated, electron-multiplying, linear-gain CCD (QuantEM, Photometrics Inc.). Dual filter wheels will be placed in front of source and detector to allow a flexible combination of multispectral reflectance and fluorescence measurements. Special care is taken with filter wheel alignment and stray light rejection in order to maximize fluorescence contrast. The Apogen light engine, QuantEM CCD camera, and both filter wheels are synchronized via the same underlying platform, developed for WiFI Instrument 1.

A custom computed tomographic imaging spectrometer (CTIS) is incorporated in the instrument in order to facilitate hyperspectral tomography and simultaneous visualization of multiple fluorophores. This instrument serves as a testbed platform for the development/visualization of tomographic algorithms and depth contrast information in the small animal ATK. The added challenge for this instrument is the 3D volumetric and cross-sectional visualization and measurement tools. This is implemented using the existing MI Inc. rendering engine based on Microsoft's Managed DirectX platform.

FIGS. 12a and 12b are schematics of WiFI Instrument 2. FIG. 12a is a block diagram of first generation small animal imaging and tomography instrument. FIG. 12b is a rendering of Apogen light-engine prototype demonstrating delivery of light via a light guide (I) onto a OMO chip (ii), which is then projected onto a target and then detected by a CCO camera (iii).

Consider now the clinic-friendly spectroscopic instrument (WiFI Instrument 3). A fast, clinic-friendly imaging instrument (WiFI Instrument 3) is fabricated for therapy guidance and wound healing monitoring. Instrument 3 is a clinic-friendly "snapshot" hyperspectral (500-1000 nm) system, capable of broadband spatial-frequency-domain imaging on a sub-second timescale. The device enables mapping of the spatial distributions of hemoglobin, lipid, water, and tissue scattering in layered tissue systems. This lightweight system is mounted on an articulating arm to allow arbitrary positioning for a variety of clinical applications, including flap and diabetic wound monitoring, melanoma studies, and port-wine stain imaging. The key component of this system is a custom holographic computed tomographic imaging spectrometer (CTIS), built by Jet Propulsion labs. In combination with the requested 2K×4K Dalsa 11M04 camera, the 7-order filter will provide ~5 nm spectral resolution of absorption and scattering across the entire spectral range from 500-1000 nm, all with only three phase projection images. This allows snapshot clinical measurements and multiple chromophore map extraction before, during, and after therapies with minimal motion artifacts or discomfort to the patient. The projection subsystem is comprised of a separate DMD light engine from Apogen geared toward lightweight construction (no filter wheels, magnesium exoskeleton, and fiber light guide tungsten source delivery), and designed for integration with the CTIS/Dalsa imaging arm. The Apogen light engine and Dalsa Pantera 11 M04 camera are synchronized via the same underlying platform developed for WiFI Instruments 1 and 2. This system is initially constructed with a liquid crystal tunable filter (LCTF), which can be replaced with the CTIS. A graphics processor unit (GPU) is provided for acceleration of the CTIS tomographic reconstruction code. While acquisition with the proposed system is <1 s, the CTIS reconstruction step is currently limited to >1 min/image for a total of >3 min computational time. While this delay in feedback is acceptable for longitudinal studies of chronic disease progression and therapeutic response, it is incompatible with applications geared at informing a physician while monitoring an acute therapy, such as port-wine stain treatment, and resection of cancerous tissues in brain, melanoma, and breast cancer surgeries. We utilize the programmable, massively data-parallel nature of GPUs to solve the CTIS expectation-maximization (EM) problem (a naturally-parallel algorithm). This is implemented using the CUDA programming model by nVidia, an abstracted set of floating-point libraries aimed at general purpose GPU computation (GPGPU). Preliminary reconstructions of CTIS data have yielded long reconstruction times (1 minute per image). A work station with GPUs will reduce the reconstruction time of the CTIS to allow near real time (1 fps) quantitative hyper-spectral imaging.

Figure 13A:
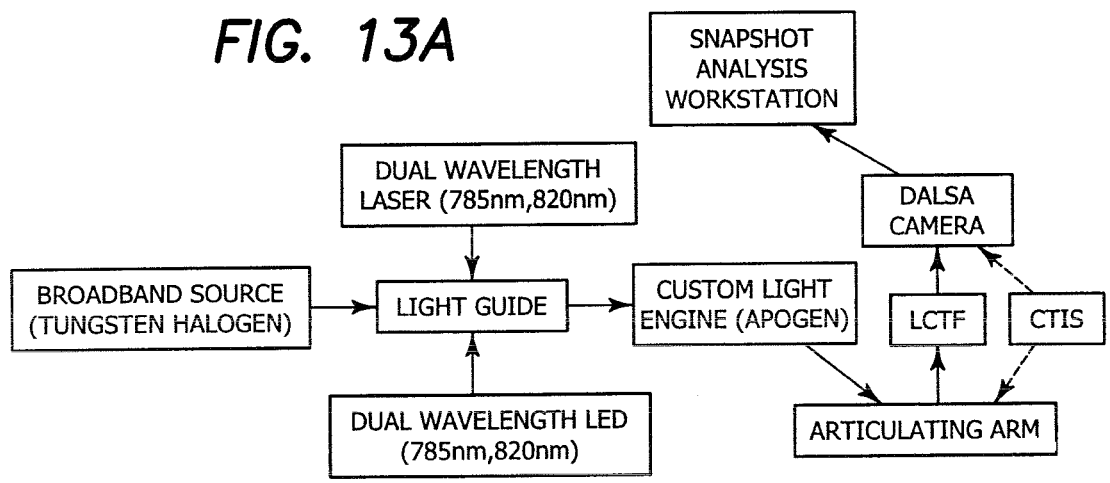
FIG. 13a is schematic of WiFI Instrument 3, which is a clinic-friendly imaging instrument.
Figure 13B:
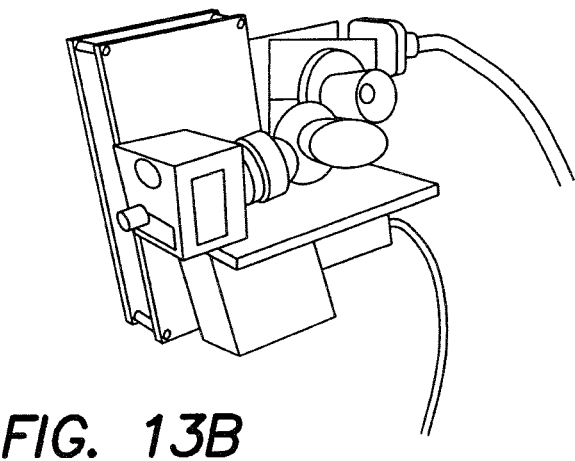
FIG. 13b is photograph of an embodiment of the clinical device of FIG. 13a with the light engine mounted on articulated arm and with real-time visualization.

FIGS. 13a and 13b are schematics of WiFI Instrument 3. FIG. 13a is a block diagram of clinic-friendly imaging instrument. FIG. 13b is an embodiment of a clinical device with the light engine mounted on articulated arm and with real-time visualization.

Thus, there are three distinct versions of the WiFI instrumentation platform (shown as FIG. 14, Table 2) provided as examples. Each has features that focus on specific pre-clinical and clinical applications.

Consider the preclinical potential of the WiFI platform to study essential quantitative hemodynamic, metabolic, and cellular processes in vivo Introduction. The objective is to investigate disease progression through acute and chronic models of ischemic stroke, epilepsy (instrument 1) and tumor angiogenesis (Instrument 2) while quantifying therapeutic response to neuroprotective agents and chemotherapies. Our approach involves application of the instruments towards animal models. It is our expectation that these studies will establish WiFI instrumentation as an absolute quantitative tool of metabolic and molecular reporter activity in animal studies.

The neuroimaging instrument (WiFI Instrument 1) can be applied in studies of epilepsy and ischemic stroke. In the epilepsy research, the objective is to study cellular swelling associated with seizure events using WiFI generated maps of reduced scattering coefficient. Such an approach is expected to have substantial advantages over the gold-standard method of EEG recordings, which are invasive and limited in number of spatial samples. A fluorescence-based method is essentially a point measurement at a discrete time point; thus, interrogation of optical property dynamics with high spatial resolution is impractical to assess. We coregister optical images with both the EEG and fluorescence-based recordings to assess the potential of WiFI to furnish data that are predictive of epilepsy. In the collaborative ischemic stroke research, we attempt to understand both acute and chronic optical changes in neurovascular coupling after the onset of ischemic stroke. The small animal tomographic imaging system (WiFI Instrument 2) is utilized for studies of tumor angiogenesis and chemotherapy monitoring in small animal models. In these studies, we determine the viability of using exogenous fluorescence contrast agents to track tumor growth and treatment. We also have the potential to learn more about the efficacy of certain chemotherapeutic agents as well as learn more about contrast agent dynamics.

TABLE 3

Preclinical validation studies

| Instrument | Clinical Problem | Objective |
| --- | --- | --- |
| Real-time Optical Neuroimaging (Instrument 1) | Epilepsy | Co-register brain electrical signals with optical scattering dynamics |
| | Ischemic Stroke | Study long-term dynamics of cortical function and metabolic activity in response to ischemic stroke |
| Small Animal Tomographic Imaging Instrument (Instrument 2) | Tumor Angiogenesis | Study dynamics of optical biomarkers related to tumor growth |
| | Chemotherapy Monitoring | Visualize changes in optical contrast during chemotherapy treatment |

We expect that valuable insight regarding the role of optical wide-field imaging in pre-clinical animal models for disease progression and therapeutic monitoring will be realized. We are in the position to impact the fields of: 1) neuroimaging, by studying neurovascular and metabolic physiology and development of neuroprotective therapies for diseases such as epilepsy and stroke, as well as 2) tumor biology, by studying the metabolic and angiogenic properties of cancer while monitoring and developing chemotherapeutic strategies for treatment.

The clinical potential of the WiFI platform as a noninvasive diagnostic and therapy monitoring tool is shown in a series of in vivo clinical studies. The objectives are to determine the efficacy of WiFI instrumentation as a quantitative therapeutic monitoring and characterization tool in clinical scenarios. Our approach involves implementation of our clinic-friendly instrument (WiFI Instrument 3) to conduct studies involving both therapy guidance (port wine stain, neurosurgery, skin cancer), and characterization of wound healing (port wine stain, flap monitoring, diabetic ulcers) in pre-clinical and clinical models. It is our expectation that these studies will collectively justify the need for an integrated WiFi instrument as a noninvasive tool for near real-time and quantitative feedback in clinical therapeutic treatment and diagnostics.

A summary of the clinical studies is presented below (Table 4).

TABLE 4

Clinical Validation Studies

| Clinical Problem | Objective |
|---|---|
| Skin Flap & Wound Healing | Quantify chronic wound healing response |
| Port wine stain | Surgical guidance for laser therapy of port wine stain birthmarks |
| Melanoma | Early detection of melanoma |
| Tumor resection | Intra-operative tumor delineation using Exogenous Fluorophores |
| Cancer Treatment | Imaging and treatment of cancer using nanorods |
| Neurosurgical Guidance | Intra-operative brain tumor delineation |

A skin flap wound healing project has already been established in collaboration with MI Inc. and is facilitated by WiFI Instrument 3. The central aim of this project is to employ WiFI to spatially resolve functional tissue characteristics in an animal wound model. Our hypothesis is that WiFI instrumentation can effectively work to provide quantitative assessment of metabolic activity within ischemic chronic wounds of superficial tissues. Although this is a pre-clinical model, this study serves as validation of our instrument to perform snapshot spectroscopy in vivo. The knowledge regarding wound healing from this study is expected to lead into a clinical study of patients with diabetic ulcers. In addition, work in the field of port wine stains will drive the study of WiFI as a therapeutic guidance tool. The Surgery Laser Clinic affiliated with BLI serves as a test-bed for clinical monitoring of port wine patients before, during, and after therapeutic treatment. Our hypothesis is that this multi-modality SI instrument can serve as an imaging platform for quantitative characterization of benign and malignant melanocytic skin lesions. A clinic ready SI-based spectral imaging system for quantitative measurements of cutaneous melanocytic lesions is provided. Once this system is optimized, we acquire and analyze MI data from patients with benign pigmented lesions and those with cutaneous melanoma who are scheduled to undergo treatment at the CHAO Family Comprehensive Cancer Center Melanoma Clinic at UC-Irvine. Finally we compare vascular parameters obtained from WiFI data with those derived from histology.

A combined fluorescence/SI instrument to provide a widefield image-guided surgical tool for tumor margin delineation is being provided. Validation studies in small animals are conducted to validate this instrument. Active targeting and selective nano-photothermolysis of nanorods in small animal models are monitored with this system.

Finally, in addition to the preclinical neurobiology studies, we are already incorporating the SI component of WiFI into a clinical neurosurgical microscope. Our goal is to evaluate the capability of WiFI to perform quantitative intraoperative brain mapping and provide information on subsurface composition. Applications include identifying eloquent neural tissue, localizing epileptic foci, and delineating tumor margins. In addition, because WiFI is a non-contact method with quantitative near-real-time visualization, it can be coregistered with intraoperative MRI to provide a complementary view of neuro-anatomic structure and function.

Insight gained regarding WiFI's potential as a medical diagnostic imaging instrument is expected. Because of its rich metabolic information content, noncontact geometry, and wide interrogation field, we anticipate WiFI can be used in a broad range of clinical settings as a powerful method for therapeutic guidance.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A method for imaging of mean particle motion of a particle moving in a turbid medium at each point in a three dimensional wide field of view of the turbid medium using an apparatus for providing structured illumination and for providing coherent illumination comprising:

imaging the particle motion in the turbid medium using the apparatus for providing structured illumination imaging using different illumination spatial frequencies of the turbid medium by the apparatus to derive static optical properties of the turbid medium;
   imaging the particle motion in the turbid medium using the apparatus for providing temporally coherent illumination imaging to derive dynamic motion of the particle in the turbid medium; and
   using a computer to generate an estimate of particle motion at each point using a correlation function model for particle motion in terms of dynamic scattering as measured by a time correlation technique including speckle contrast indicative of speckle blurring.

2. The method of claim 1 further comprising using the apparatus for performing both structured illumination imaging and temporally coherent illumination imaging to simultaneously derive static optical properties and dynamic motion using a spatially structured coherent source.

3. The method of claim 2 where the turbid medium is tissue and where using the apparatus for performing structured illumination imaging with structured coherent illumination to derive static optical properties and dynamic motion comprises measuring blood flow in vivo in the tissue with one or more structured illumination conditions.

4. The method of claim 3 further comprising using the computer to generate a blood flow map in vivo in tissue.

5. The method of claim 1 further comprising using the computer to measure tissue oxygenation and perfusion in tissue.

6. The method of claim 5 further comprising using the computer to measure healing failure in a chronic wound in peripheral vascular disease, diabetic ulcer or pressure ulcer.

7. The method of claim 2 where using the apparatus for performing both structured illumination imaging and temporally coherent illumination imaging to simultaneously derive static optical properties and dynamic motion using a spatially structured coherent source comprises:

using the apparatus for performing both structured illumination imaging with laser speckle imaging to simultaneously derive optical properties and speckle contrast at different spatial frequencies of the turbid medium by:
      storing in a memory the three structured illumination images at each spatial frequency;
      using the computer to calculate a mean intensity map, $<I>$, with a sliding window, for each of three structured illumination images stored in the storage medium;
      using the computer to generate a single demodulated mean intensity image from intensity values of the three stored structured illumination images;
      using the computer to convert the single demodulated intensity image to a mean diffuse reflectance image using a calibration process; and
      using the computer to convert the mean diffuse reflectance image by an inverse process into maps of absorption and reduced scattering coefficient;
      using the computer to generate a standard deviation, $\sigma$ map, with a sliding window, for each of the three stored structured illumination images;
      using the computer to generate a single demodulated $\sigma$ image from the three standard deviation, $\sigma$ maps; and
      using the computer to generate a speckle contrast, K, map by dividing the single demodulated $\sigma$ image, with the single demodulated mean intensity image,
   so that the map of the estimate of particle motion at each point using the correlation function model for particle motion in terms of dynamic scattering as measured in speckle contrast is then generated to obtain a measure of particle motion by separating static and dynamic optical absorption components.

8. The method of claim 1 further comprising modulating the structured illumination imaging using speckle laser illumination to obtain depth resolved imaging of speckle contrast.

9. An apparatus for imaging of mean particle motion in a turbid medium at each point in a wide field of view of a turbid medium comprising:

means for performing both structured illumination imaging using speckle laser illumination in combination with laser speckle imaging to simultaneously derive optical properties and speckle contrast at different spatial frequencies of the turbid medium; and
   means for generating an estimate of particle motion at each point using a correlation function model for particle motion in terms of dynamic scattering as measured in speckle contrast.

* * * * *